(12) United States Patent
Worthington et al.

(10) Patent No.: US 7,366,063 B2
(45) Date of Patent: Apr. 29, 2008

(54) OPTICAL DISCS FOR MEASURING ANALYTES

(75) Inventors: Mark O. Worthington, Irvine, CA (US); James R. Norton, Santa Ana, CA (US); Horacio Kido, Niland, CA (US); Victor M. Ortiz, Orange, CA (US)

(73) Assignees: Burstein Technologies, Inc., Irvine, CA (US); Nagaoka & Co., Ltd., Hyogo (JP)

( * ) Notice: Subject to any disclaimer, the term of this patent is extended or adjusted under 35 U.S.C. 154(b) by 91 days.

(21) Appl. No.: 11/458,335

(22) Filed: Jul. 18, 2006

(65) Prior Publication Data

US 2006/0250930 A1    Nov. 9, 2006

Related U.S. Application Data

(63) Continuation of application No. 10/005,313, filed on Dec. 7, 2001, now Pat. No. 7,079,468.

(60) Provisional application No. 60/323,405, filed on Sep. 19, 2001, provisional application No. 60/306,226, filed on Jul. 18, 2001, provisional application No. 60/303,437, filed on Jul. 6, 2001, provisional application No. 60/294,051, filed on May 29, 2001, provisional application No. 60/294,052, filed on May 29, 2001, provisional application No. 60/293,917, filed on May 24, 2001, provisional application No. 60/255,233, filed on Dec. 12, 2000, provisional application No. 60/254,394, filed on Dec. 8, 2000.

(51) Int. Cl.
*G11B 7/00* (2006.01)

(52) U.S. Cl. .............................. 369/44.14; 369/44.25; 369/112.01; 369/112.1

(58) Field of Classification Search ..................... None
See application file for complete search history.

(56) References Cited

U.S. PATENT DOCUMENTS 6,030,581 A    2/2000    Virtanen

FOREIGN PATENT DOCUMENTS

AU    714662    4/1996

(Continued)

OTHER PUBLICATIONS

Tibbe et al. (1999) Optical tracking and detection of immunomagnetically selected and aligned cells. Nature Biotechnology. 17:1210-1213.

(Continued)

*Primary Examiner*—Muhammad Edun
(74) *Attorney, Agent, or Firm*—Knobbe Martens Olson & Bear, LLP

(57) ABSTRACT

This invention directs to an optical disc assembly configured to receive an analyte which can be detected by a standard optical disc reader or an optical disc reader modified therefrom. The optical disc assembly may preferably be designed so that the optical disc reader can track the disc and detect the analyte concurrently and discriminably. The optical disc assembly contains or encodes optically readable features which are trackable by the optical disc reader and which have encoded speed information enabling the optical disc reader to rotate the optical disc assembly at a determinable speed. The optical disc assembly also includes an analyte section capable of receiving the analyte that can be detected by the optical disc reader.

22 Claims, 20 Drawing Sheets

FOREIGN PATENT DOCUMENTS

| | | |
|---|---|---|
| AU | 39585/97 | 2/1998 |
| DE | 19938839 A1 | 8/2000 |
| DE | 10037687 A1 | 2/2002 |
| EP | 0297394 A2 | 1/1989 |
| EP | 0392475 A2 | 10/1990 |
| EP | 0417305 A1 | 3/1991 |
| EP | 0430248 A2 | 6/1991 |
| EP | 0435246 A2 | 7/1991 |
| EP | 0504432 A1 | 9/1992 |
| EP | 0521421 A2 | 1/1993 |
| EP | 0693560 A2 | 1/1996 |
| EP | 0703825 B1 | 7/1997 |
| EP | 0866449 A2 | 9/1998 |
| EP | 0608006 B1 | 3/1999 |
| GB | 2337113 | 3/2001 |
| JP | 10083571 A | 3/1998 |
| JP | 2001110060 A | 10/1999 |
| WO | WO 93/22053 | 11/1993 |
| WO | WO 94/29484 | 12/1994 |
| WO | WO 95/33986 | 12/1995 |
| WO | WO 96/04547 | 2/1996 |
| WO | WO 96/09548 | 3/1996 |
| WO | WO 96/17959 | 6/1996 |
| WO | WO 97/18558 | 5/1997 |
| WO | WO 97/18559 | 5/1997 |
| WO | WO 97/21090 | 6/1997 |
| WO | WO 98/01533 | 1/1998 |
| WO | WO 98/01857 | 1/1998 |
| WO | WO 98/01858 | 1/1998 |
| WO | WO 98/07019 | 2/1998 |
| WO | WO 98/12559 | 3/1998 |
| WO | WO 98/15356 | 4/1998 |
| WO | WO 98/32535 | 7/1998 |
| WO | WO 98/37238 | 8/1998 |
| WO | WO 98/37555 | 8/1998 |
| WO | WO 98/38510 | 9/1998 |
| WO | WO 98/45693 | 10/1998 |
| WO | WO 98/53311 | 11/1998 |
| WO | WO 99/32663 | 7/1999 |
| WO | WO 99/35499 | 7/1999 |
| WO | WO 99/58245 | 11/1999 |
| WO | WO 99/61461 | 12/1999 |
| WO | WO 00/05582 | 2/2000 |
| WO | WO 00/20838 | 4/2000 |
| WO | WO 00/26677 | 5/2000 |
| WO | WO 00/78455 A1 | 12/2000 |
| WO | WO 01/02737 A1 | 1/2001 |
| WO | WO 01/43938 A1 | 6/2001 |
| WO | WO 01/46465 A2 | 6/2001 |
| WO | WO 01/47638 A2 | 7/2001 |
| WO | WO/0147637 A1 | 7/2001 |
| WO | WO 01/87485 A2 | 11/2001 |
| WO | WO 01/87486 A2 | 11/2001 |
| WO | WO 01/87487 A2 | 11/2001 |
| WO | WO 01/87768 A2 | 11/2001 |
| WO | WO 02/06836 A2 | 1/2002 |
| WO | WO 02/42498 A2 | 5/2002 |

OTHER PUBLICATIONS

Tibbe et al. (2000) Cell Analysis System Based on Immunomagnetic Cell Selection and Alignment Followed by Immunofluorescent Analysis Using Compact Disk Technologies. Cytometry. 43:31-37.

Benschop et al. (1991) Confocal compact scanning optical microscope based on compact disc technology. Applied Optics. 30 (10):1179-1184.

Schembri et al. (1995) Centrifugation and capillarity integrated into a multiple analyte whole blood analyzer. J. Automatic Chem. 17(3):99-104.

Burtis et al. (1980) Data processing for centrifugal analyzers. Centrifugal Analysers in Clinical Chemistry. 51-69.

DeRisi et al. (1997) Exploring the Metabolic and Genetic Control of Gene Expression on a Genomic Scale. Science. 278:680-686.

Duffy et al. (1999) Microfabricated Centrifugal Microfluidic Systems: Characterization and Multiple Enzymatic Assays. Anal. Chem. 71:4669-4678.

Pfahler, J. (1992) Liquid Transport in Micron and Submicron Size Channels: A Dissertation in Mechanical Engineering and Applied Mechanics.

Freemantle, Mi. (1997) Photochemical Strategy Patterns Nanoparticles. C&EN. 9.

Konings, et al. (1996) Deconvoluation of Combinatorial Libraries for Drug Discovery: Theoretical Comparison of Pooling Strategies. J. Med. Chem. 39:2710-2719.

Schild, D. (1996) Laser Scanning Microscopy and Calcium Imaging. Cell Calcium 19(4):281-296.

Given, A.L. (1992) Flow Cytometry First Principles. Wiley-Liss, New York, N.Y.

Gosling et al. (1994) Immunoassay: Laboratory Analysis and Clinical Applications. Butterworth-Heinemann, Newton, Massachusetts.

Green, F. (1991) The Sigma-Aldrich Handbook of Stains, Dyes and Indicators. Aldrich Chemical Company, Inc., Milwaukee, Wisconsin.

International Preliminary Examination Report for PCT/US01/46175, May 13, 2003.

International Search Report for PCT/US01/46175.

US 7,366,063 B2

OPTICAL DISCS FOR MEASURING ANALYTES

This application is a continuation of U.S. application Ser. No. 10/005,313, filed on Dec. 7, 2001 now U.S. Pat. No. 7,079,468, which claims priority from U.S. Provisional Application Ser. No. 60/254,394, filed Dec. 8, 2000; U.S. Provisional Application Ser. No. 60/255,233, filed Dec. 12, 2000; U.S. Provisional Application Ser. No. 60/293,917, filed May 24, 2001; U.S. Provisional Application Ser. No. 60/294,051, filed May 29, 2001; U.S. Provisional Application Ser. No. 60/294,052, filed May 29, 2001; U.S. Provisional Application Ser. No. 60/303,437, filed Jul. 6, 2001; U.S. Provisional Application Ser. No. 60/306,226, filed Jul. 18, 2001; and U.S. Provisional Application Ser. No. 60/323,405, filed Sep. 19, 2001, which are hereby incorporated in their entirety by reference herein.

FIELD OF THE INVENTION

This invention relates to optical discs configured to receive analytes which can be detected by a standard optical disc reader or an optical disc reader modified therefrom.

BACKGROUND OF THE INVENTION

Optical discs have been used for detection and characterization of biological and chemical samples. For instance, see WO 96/09548 (Gordon), EP A 392475 (Idemitsu), EP A 417 305 (Idemitsu), EP A 504432 (Idemitsu), and WO 98/12559 (Demers), all of which are incorporated herein by reference. Other examples of using optical discs to detect investigational samples can be found in U.S. Provisional Application 60/252,725, entitled "Optical Bio-Disc Including Microfluidic Circuit For Separation And Quantification Of Agglutinated Microparticles Or Cells And Methods Relating Thereto," U.S. Provisional Application No. 60/252,726, entitled "Bioactive Solid Phase For Specific Cell Capture And Optical Bio-Disc Including Same," and U.S. Provisional Application No. 60/257,705, entitled "Surface Assembly For Immobilizing DNA Capture Probes And Bead-Based Assay Including Optical Bio-Discs And Methods Relating Thereto," all of which are incorporated herein by reference.

These previously described optical discs, however, are not designed to be read by standard optical disc readers, such as standard CD or DVD readers. For instance, the optical discs disclosed in EP A 392475 (Idemitsu), EP A 417 305 (Idemitsu) and EP A 504432 (Idemitsu) require the use of two optical detectors, one to detect the tracking information and the other to detect surface structures. In contrast, reading a standard CD or DVD needs only one optical detector.

Therefore, there is a need to design and manufacture an optical disc configured to receive an investigational sample which can be detected by a standard optical disc reader or an optical disc reader modified therefrom.

Over the past decade, scanning laser microscopy (SLM) has revolutionized life science imaging. However, SLM demands expensive and specialized optical equipment. Consequently, there exists a need to provide an inexpensive, generic device which can carry out laser scanning over microscopic specimens.

The present invention discovers that the minimum mechanical requirements for SLM, i.e. laser, focusing and detection optics, precision scanning means, and computer interface, may all be provided by a standard optical disc reader or an optical disc reader modified therefrom. Therefore, it is desirable to create an optical disc which can hold a microscopic sample that can be scanned by a standard optical disc reader. Such an optical disc presents a marked advantage over existing SLM technologies.

In order for a standard optical disc reader to operate an optical disc, the optical disc reader is typically required to be able to (1) accurately focus above the operational surface of the optical disc, (2) accurately follow the spiral track or utilize some form of uniform radial movement across the optical disc surface, (3) recover enough information to facilitate a form of speed control, such as CAV, CLV, VBR, CBR, or ZCLV, (4) maintain proper power control by logical information gathered from the optical disc or by signal patterns detected in the operational surface of the optical disc, and (5) respond to logic information that is used to control, for example, the position of the objective assembly, the speed of rotation or the focusing position of the laser beam.

A typical optical disc system uses elements of the optical medium itself to satisfy at least some of these operational requirements. For instance, in a typical CD, the disc substrate is impressed with a spiral track made up of a series of embossed or impressed pits and lands. Light reflected from these pits and lands can be used to generate signals. These signals are used by the optical disc reader to maintain proper focusing and tracking. In a CD-R disc, a wobble groove is used to generate operational signals during disc recording. Dye marks are created during disc recording, and these dye marks may provide the requisite tracking structures during subsequent reading. Generally, under each of conventional optical disc standards, the structures that encode data may simultaneously serve to provide operational signals that enable an optical disc reader to operate the optical disc.

Conventional optical disc standards make no provision with respect to acquisition of information from investigational features, such as biological or chemical specimens, that are disposed on the disc. Investigational features disposed on the disc may disrupt the tracking of the disc. In addition, investigational features may be sufficiently separated from operational structures, therefore preventing an optical disc reader from tracking the disc and detecting the investigational features concurrently and discriminably.

Therefore, there is a need to provide an optical disc which allows an optical disc reader to detect the investigational features without disrupting the tracking of the disc. There also exists a need to provide an optical disc which allows an optical disc reader to track the disc and read the investigational features concurrently and discriminably.

SUMMARY OF THE INVENTION

In one embodiment, an optical disc assembly is configured to associate with an analyte which can be detected by a standard optical disc reader or an optical disc reader modified therefrom.

In another embodiment, an optical disc assembly is configured to associate with an analyte, and the association with the analyte does not prevent an optical disc reader from tracking the disc assembly.

In yet another embodiment, an optical disc assembly, which is associated with an analyte, is configured to enable an optical disc reader to track the disc assembly and detect the analyte concurrently and discriminably.

In accordance with one aspect of this invention, the optical disc assembly includes (1) optically readable structures which are trackable by an optical disc reader and which have encoded speed information enabling the optical disc reader to rotate the optical disc at a speed that is determinable from the speed information; and (2) an analyte section capable of receiving an analyte which can be detected by the optical disc reader. The optically readable structures may be impressed in the operational surface and coated with a reflective layer. The optical disc reader may be a CD or DVD reader. The optically readable structures can be in a CD format or a DVD format.

The analyte section may include at least one analyte chamber located within the disc assembly, such as between the operational layer and another layer of the disc assembly. At least one channel may be created in one of the layers of the disc assembly to allow the analyte or other components to enter or exit the analyte chamber. The channel may include a valve regulated by optically readable data encoded in the optical disc assembly. In one embodiment, the analyte section includes a plurality of analyte chambers, each chamber being connected to at least a channel.

In one embodiment, design information of the optical disc assembly is encoded in the disc assembly.

In another embodiment, the disc assembly is a reverse disc including a lens layer capable of focusing the laser beam on the operational surface which is located at the laser-proximal surface of the operational layer.

In yet another embodiment, the operational surface in the reverse disc includes a cut-away area which either lacks operational structures or includes modified operational structures. In addition, the cut-away area may lack reflective coatings.

In a preferred embodiment, the analyte chamber includes a surface which is located within 15 micrometers from the operational surface, preferably located within 15 micrometers from the cut-away area, and which preferably is capable of receiving the analyte.

In another preferred embodiment, the disc assembly is a forward disc. The operational surface is at the laser-distal surface of the operational layer and coated with a semi-transmissive, semi-reflective layer. There is a second layer which is laser-distal to the operational layer and which is coated with another reflective layer. Preferably, the operational surface includes a cut-away area, and the analyte chamber includes a surface which is located within 15 micrometers from the cut-away area. More preferably, the analyte chamber includes the cut-away area. The second layer may lack optically readable structures that have encoded tracking information.

In one embodiment, the analyte section contains the analyte which may be a biological or chemical sample. Preferably, the analyte is located within 15 micrometers from the operational surface.

In yet another embodiment, the analyte section is embedded in the disc assembly and includes a surface which is located within 15 micrometers from the operational surface and which preferably is capable of receiving the analyte.

In one embodiment, the disc assembly has encoded information for conducting an assay on the analyte.

In accordance with yet another aspect of this invention, the optical disc assembly includes (1) a hologram which contains optically readable features that have encoded (a) tracking information, and (b) speed information enabling an optical disc reader to rotate the optical disc at a speed that is determinable from the speed information; and (2) an analyte section capable of receiving an analyte which can be detected by the optical disc reader. The hologram may be reflective or replaceable. The optical disc reader may be a CD or DVD reader.

In one embodiment, at least part of the image plane of the hologram is located within the analyte section. The analyte section may include the analyte which may be positioned within 15 micrometers from the image plane of the hologram. The laser beam may be focused on the image plane of the hologram.

In accordance with another aspect of this invention, an analyte held in the analyte section of the optical disc assembly is detected using a CD or DVD reader. The detection includes the steps of (1) introducing the optical disc assembly into the CD or DVD reader; (2) reading the optically disc assembly; and (3) obtaining a signal which is indicative of the presence of the analyte. Preferably, the signal thus obtained is a quad sum signal.

BRIEF DESCRIPTION OF THE DRAWINGS

All the drawings used herein are given by way of illustration, not limitation, and all the drawing are not drawn to scale.

DESCRIPTION OF EMBODIMENTS OF THE INVENTION

Figure 1:
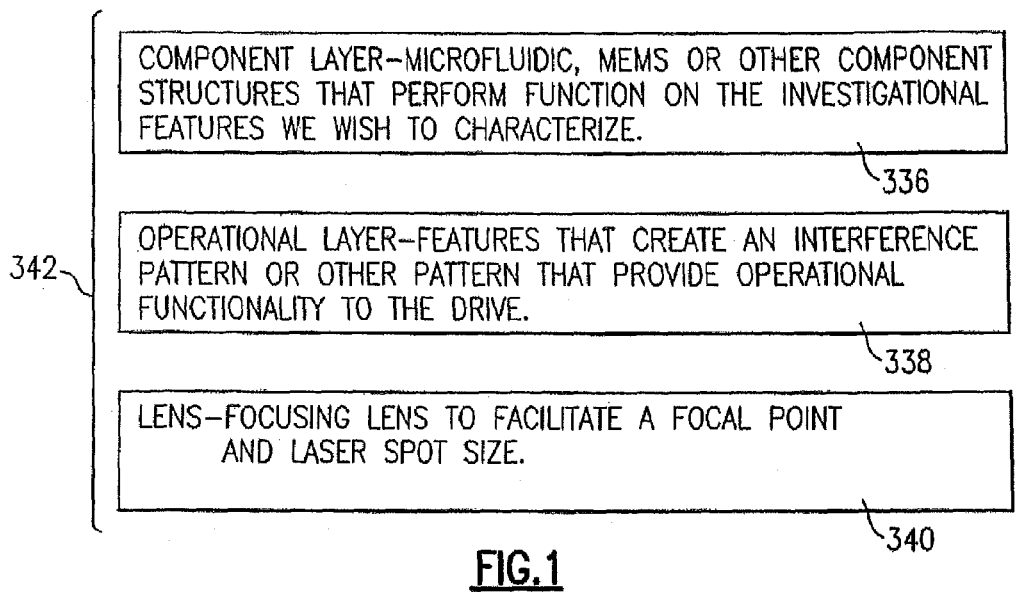
FIG. 1 demonstrates the functional components of an optical disc assembly according to one embodiment of the present invention.

This invention relates to an optical disc assembly configured to receive an analyte of interest which can be detected by an optical disc reader. The analyte of interest may be a physical specimen, such as a biological, chemical, or biochemical specimen, or a product produced by a biological or chemical reaction carried out in the optical disc assembly. The optical disc reader may be a CD reader or a DVD reader. The optical disc reader may be a standard optical disc reader or an optical disc reader modified therefrom. The optical disc assembly may be designed so that the association of the analyte with the disc assembly does not prevent the optical disc reader from tracking the disc assembly or performing other operational functions.

As used herein, various surfaces in an optical disc assembly can be numbered or named according to the order in which the light beam of the optical disc reader strikes or passes through them upon first occurrence. For example, when a compact disc (CD) is read by a CD reader, the laser beam of the CD reader first enters the disc through a surface of a polycarbonate layer. The polycarbonate layer also is known as the polycarbonate disc or the substrate. This surface is referred to as the first surface or the laser-proximal surface of the polycarbonate layer. The laser beam proceeds through the polycarbonate layer and comes out through another surface of the polycarbonate layer. This latter surface is referred to as the second or the laser-distal surface of the polycarbonate layer. The laser beam proceeds to a reflective layer which is usually made of gold or other reflective material. The reflective layer is laser-distal to the polycarbonate layer. The laser beam is reflected back from the reflective layer, passing through the polycarbonate layer and entering a detector in the CD reader.

When a CD-R disc is read by a CD-R reader, the laser beam of the reader enters the CD-R disc through the first surface of a polycarbonate layer. The laser beam proceeds through the polycarbonate layer and enters into a dye layer which is laid on the tracks embossed or impressed in the laser-distal surface of the polycarbonate layer. The polycarbonate layer is laser-proximal to the dye layer. The back surface of a CD-R disc, upon which labels or markings are laid, is referred to as the back plane. The back plane is the most laser-distal surface in the CD-R disc.

As used herein, "operational structures" or "operational features" in an optical disc assembly refer to optically readable structures which are impressed or encoded in the optical disc assembly and which enable an optical disc reader to track, synchronize, or perform other customized operational functions. Operational structures may act as phase components or provide interference patterns. Operational structures may have encoded speed information that enables the optical disc reader to rotate the disc assembly at a speed determinable from the speed information. Light returned from or passed over operational structures can be acquired by the optical disc reader to generate operational signals. These operational signals are used by the optical disc reader to track, focus, synchronize, or perform other operational functions.

Operational structures may be imprinted or impressed in a surface of a layer in the disc assembly. Such a layer is referred to as an "operational layer," and such a surface is referred to as an "operational surface." In a typical CD disc, the operational layer is the polycarbonate disc, and the operational surface is the laser-distal surface of the polycarbonate disc. An optical disc assembly may have more than one operational layer or operational surface. Preferred operational structures include, but are not limited to, wobble grooves, pits and lands, dye marks, or any combination thereof.

Operational structures may be encoded in a hologram. Light returned from or transmitted through the hologram can create an image plane within which the encoded operational structures appear to be positioned. The encoded operational structures, as appeared in the image plane of the hologram, preferably are in the form of wobble grooves, tracks of pits and lands, or any other type of operational structures that may be physically impressed in an optical disc's operational layer.

Operational structures, impressed or encoded, may be in a variety of formats. Suitable formats for this invention include, but are not limited to, CD formats, DVD formats, any combination thereof, or other optical disc formats. CD formats include, but are not limited to, CD-ROM, CD-R and CD-RW formats. DVD formats include, but are not limited to, DVD-R, DVD-RW and DVD-RAM formats. As appreciated by one of skill in the art, other CD or DVD formats or other optical disc formats, including those that have been or will be developed in the future, may be used in the present invention.

"Investigational structures" or "investigational features" refers to the structures, features or items that are placed in an optical disc assembly to be examined. An investigational structure or feature may be an analyte which includes a physical specimen, such as a biological or chemical sample, or a product produced by a biological or chemical reaction conducted in the optical disc assembly. An investigational structure or feature may also be part of an analyte. Investigational structures or features usually cannot provide operational information. Investigational structures or features typically are not imprinted or impressed in the optical disc assembly. They usually are not encoded in a hologram. Preferably, investigational structures or features are replaceably disposed in the optical disc assembly. Investigational structures or features may be chemical, biochemical, or biological in nature. They may also be signal or reporter elements such as beads.

Association of investigational structures with an optical disc assembly of the present invention does not prevent the optical disc reader from operating the optical disc assembly. In order to operate an optical disc assembly, the optical disc reader usually needs to (1) accurately focus above the operational surface of the disc assembly, (2) accurately track the operational surface or use some form of radial movement across the disc surface, (3) maintain a form of speed control, (4) maintain proper power control by logical information gathered from the disc assembly, and (5) respond to logic information that may be used to control, for example, the position of the objective assembly, the speed of rotation, or the focusing position of the laser beam.

An analyte that is disposed in the optical disc assembly of the present invention can be read or detected by an optical disc reader. As used herein, an analyte can be read or detected by an optical disc reader if the optical disc reader can generate at least a signal indicative of the presence of the analyte. The present invention also contemplates the use of the optical disc reader to generate signals indicative of other properties of the analyte, such as the concentration or dimension of the analyte.

In accordance with one aspect of the present invention, the optical disc assembly includes at least an operational layer and at least an analyte section. The operational layer contains an operational surface in which operational structures are impressed. The operational structures have encoded operational information which enables the optical disc reader to operate the disc assembly. In particular, the operational structures may have encoded tracking information that allows the disc reader to track the operational structures. The operational structures may also have encoded speed information enabling the disc reader to rotate the disc assembly at a speed determinable from the encoded speed information. Preferably, the operational structures are coated with a reflective layer containing a reflective material, such as metal, aluminum, gold, silver, or silicon. As used herein, a reflective layer can be semi-reflective and semi-transmissive. Light reflected from the reflective layer can be acquired by the disc reader to generate operational signals for focusing, tracking, or performing other operational functions. The operational layer may be a hologram in which the operational structures are encoded.

Speed information encoded in the operational structures allows an optical disc reader to rotate the optical disc assembly at a determinable speed. Speed information may be encoded in frame synchronization words which allow the optical disc reader to adjust the disc speed to keep a desired data rate. The speed information may also be encoded in a wobble groove. The wobble groove can produce signals useful for regulating the disc speed. In addition, special marks or logic information can be used to provide speed information. In one embodiment, the optical disc reader rotates the optical disc assembly with a constant linear velocity.

The analyte section is configured to receive at least an analyte of interest. The analyte section may be embedded in the disc assembly. It may be positioned between two layers of the disc assembly. It may also be located within a layer in the optical disc assembly. As used herein, a layer in a disc assembly refers to a thickness of material. For instance, a layer may be a substrate disc or a coating of reflective material. A layer may also be an insert which can be assembled into another layer in the disc assembly. A layer may be flat or not flat. A layer may be homogeneous or non-homogenous. The depth of a layer may be uniform or not uniform. A layer may be an assembly of several parts. The analyte section may be the most laser-distal or the most laser proximal structure in the disc assembly. The analyte section may include channels, microfluidic channels, chambers, cavities, or other structures that are designed for the manipulation, creation, or retention of the analyte of interest or the investigational structure. The analyte section may also be referred to as the component layer. An optical disc assembly may have more than one analyte section. The analyte section and the operational layer can be intermixed so long as the optical disc reader can retain control of focusing, tracking, velocity and other operational functions. Analytes or investigational structures can be in the nanometer, micrometer or millimeter range, and can be disposed, modified or created in the analyte section.

Preferably, the optical disc assembly includes a lens layer. The lens layer may be used to focus the laser beam, for instance, on either the operational structures, or the investigational structures. In one embodiment, the operational layer may function as a lens layer. In such a case, the operational structures are embossed in the laser-distal surface of the operational layer. The refractive index of the lens layer can be selected to perform the desired focusing function. The lens layer typically is laser-proximal to the operational or investigational structures. Preferably, the lens layer includes a material selected from the group consisting of plastic and glass. More preferably, the lens layer consists of plastic, such as polycarbonate or polystyrene. In a highly preferred embodiment, the lens layer consists of polycarbonate. Other examples of material suitable for constructing a lens layer include polymethylacrylic, polyethylene, polypropylene, polyacrylate, polymethyl-methacrylate, polyvinylchloride, polytetrafluoroethylene, polyacetal, polysulfone, celluloseacetate, cellulosenitrate, nitrocellulose, or any mixtures or combinations thereof.

The optical disc assembly of the present invention preferably approximates the dimensions of a unitary disc. For instance, the disc assembly may have a radial diameter between about 110 mm and 130 mm, including the range from 75 mm to 85 mm, and preferably 120 mm. Preferably, the disc assembly has a depth or thickness between about 0.8 mm and 2.4 mm, such as between 1.0 mm and 1.4 mm. More preferably, the disc assembly has a depth or thickness between 1.1 mm and 1.3 mm, including 1.2 mm. In one embodiment, the disc assembly may have a thickness of about 0.6 mm. The disc assembly may be flat or not flat, circular or non-circular. The disc assembly may have a central hole through which the disc assembly can be coupled to a disc reader.

With reference to FIG. 1, there is shown a diagram illustrating one embodiment of the present invention. The optical disc assembly has at least an operational layer 338, a component layer 336, and a lens layer 340. The disc assembly encompasses the focusing range of the laser used by the disc reader. The operational layer 338 contains the operational structures that are used by the disc reader to track the disc assembly. The operational structures may create an interference pattern or other patterns that provide operational functionality to the disc reader. The component layer 336 contains the investigational structures as well as other structures that are related to the manipulation, creation, or retention of the investigational structures. The component layer may include microfluidic channels. The lens layer 340 may focus the laser beam either on the operational structures or on the investigational structures. The component layer and the operational layer may be intermixed or overlapped so long as the disc reader can retain control of the focusing, tracking and speed. The measurement area 342 represents the area which are readable by the disc reader's laser, and the laser's focal point can roam across the measurement area. The measurement area may encompass any of the component layer, the operational layer, the lens layer, or a portion thereof.

Figure 2:
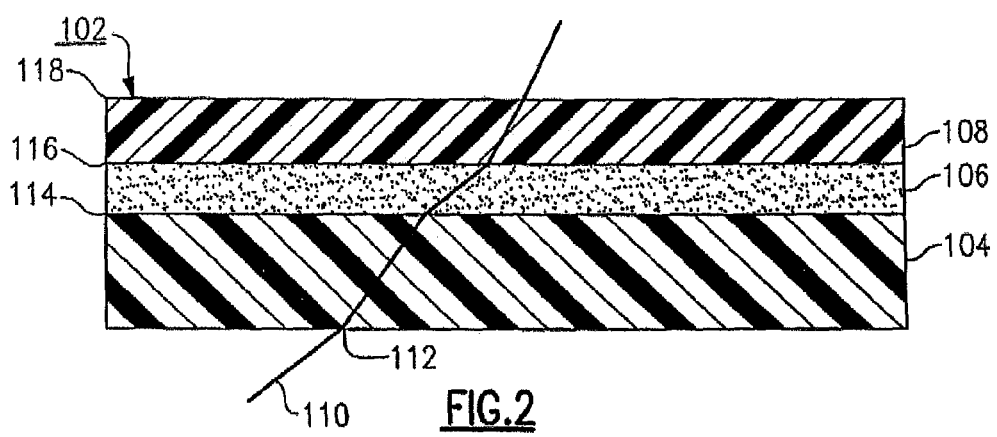
FIG. 2 shows a cross-sectional view of an optical stack including three layers of refractive material.

Different layers in an optical disc assembly may have different optical properties and can impose different optical effects on the light beam that passes through these layers. These optical effects include, for example, reflection, refraction, transmission, or absorption. FIG. 2 is a simplified example showing the effects of different layers on the passage of a light beam.

The optical disc 102 in FIG. 2 includes three layers of refractive material, 104, 106 and 108. The refractive properties of these layers may differ based on their compositions. The different refractive properties create changes in the light beam 110 as the light beam passes through these layers. The layers may be named in order of their first contact with the light beam 110. The light beam 110 enters through the bottom surface 112 and exits at the top surface 118. Therefore, layer 104 may be referred to as the most laser-proximal layer, and layer 108 as the most laser-distal layer. Layer 106 is laser-distal to layer 104, and laser-proximal to layer 108.

The light beam 110 enters layer 104 at surface 112. The light beam is bent and slowed because of the refractive property of layer 104. The light beam exits layer 104 at surface 114, and then enters layer 106 which has a different refractive property, therefore further altering the angle and speed of the light beam. As the light beam exits layer 106, it enters layer 108 at surface 116 with a further changed angle and speed. The light beam exits layer 108 at surface 118. Surface 112 is laser-proximal to surface 114 which is laser-proximal to surface 116. Surface 118 is the most laser-distal surface in the optical stack 102.

In one embodiment, the optical disc assembly is designed based on a modification of an industry standard design, such as standard CD (including CD-R and CD-RW) or a standard DVD (including DVD-RAM, DVD-R and DVD-RW). The following description is based on modifications of a standard CD-R disc. Similar modifications can be applied to other optical discs, such as CD-RW or DVD discs, as appreciated by one of ordinary skill in the art.

A normal CD-R disc contains a wobble groove utilized by the CD-R drive to spin and track the disc. A similar principal applies to a DVD-type disc. A standard CD-R disc has a polycarbonate operational layer having a depth of about 1.2 mm. The polycarbonate operational layer has at least a wobble groove embossed in the laser-distal surface of the layer. The depth of the wobble groove in a standard CD-R is approximately from 165 nanometers to 230 nanometers. A typical wobble groove is filled with dye. Above the dye layer is a reflective layer which contains gold or other reflective material such as silver. The reflective layer can reflect the laser beam of the disc drive back to a detector in the disc drive. The laser beam can be focused on the reflective layer. The laser's focus may be adjusted by a focusing servo. The wobble groove functions like a diffraction grating, and is capable of creating a pattern in the reflected laser light. The pattern in the reflected laser light is used by the disc drive to spin and track the disc. In a standard DVD disc, the wobble groove depth can be 50 nanometers.

Figure 3:
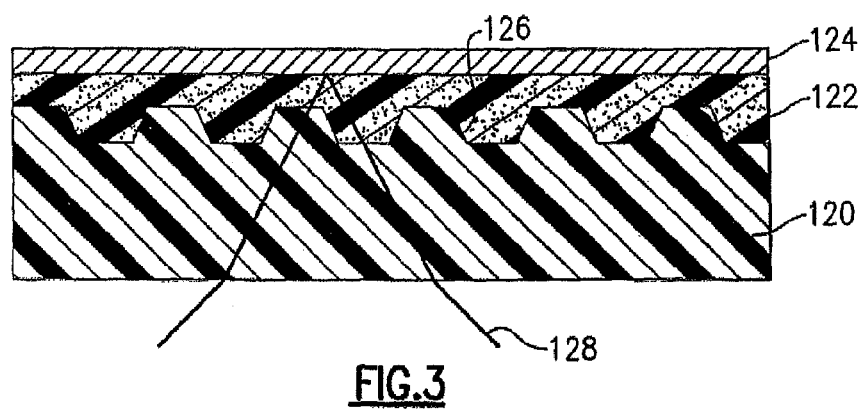
FIG. 3 is a cross-sectional view of a compact disc recordable (CD-R) including a polycarbonate layer, a dye layer, and a reflective layer.

FIG. 3 exemplifies a CD-R disc with an industry standard design. The disc has an operational layer 120 which is usually made of polycarbonate, a dye layer 122 which contains CD recordable light sensitive dye, and a reflective layer 124 which contains gold, silver or other material that is suitable for reflecting the laser beam 128 back to the detector of the disc drive. The operational layer 120 is capable of focusing the laser beam 128 on the reflective layer 124. As used herein, a layer in an optical disc is capable of focusing a reading beam of an optical disc reader on an object if the reading beam, which is directed to the object, can pass through the layer and become focused on the object while the optical disc reader is operating the optical disc. Preferably, the refractive index of the layer is significantly greater than the refractive index of air, as appreciated by one of skill in the art. For instance, the refractive index of the layer may be 1.55. Other layer or layers may also exist in the optical path of the reading beam to help the reading beam become focused on the object. The wobble groove 126 is shown in FIG. 3.

Figure 4:
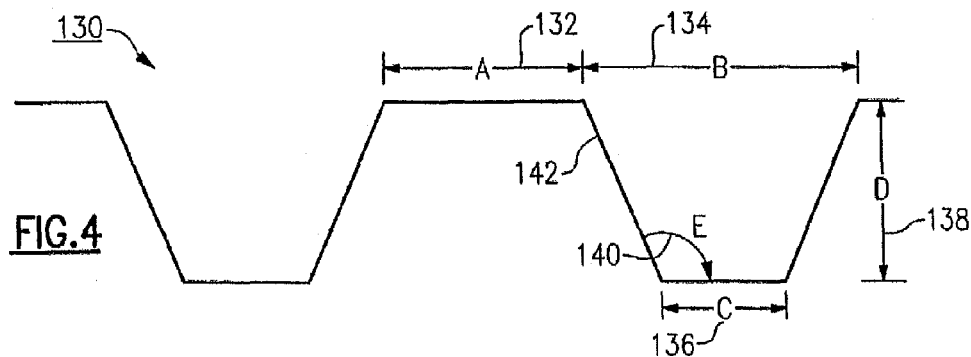
FIG. 4 is a diagram showing the geometry of a wobbled groove as it is embossed in an operational surface.

FIG. 4 demonstrates the geometry of a wobbled groove in a CD-R. As with other figures used herein, FIG. 4 is not drawn to scale. The wobble groove is usually embossed into the laser-distal surface of the operational layer in a CD-R. FIG. 4 shows two wobbled grooves. Measurement A, 132, represents the distance between two adjacent wobble grooves. Measurement B, 134, denotes the width of the top of the wobble groove. Measurement C, 136, represents the width of the bottom of the wobble groove. Measurement D, 138, shows the depth of the groove. The angle E, 140, between the side-wall 142 and the bottom of the wobble groove has an important effect on light that encounters the wobbled groove. The geometry of the wobble groove in a CD-R disc has a significant effect on the performance of the CD-R disc in a high speed writer.

Figure 5:
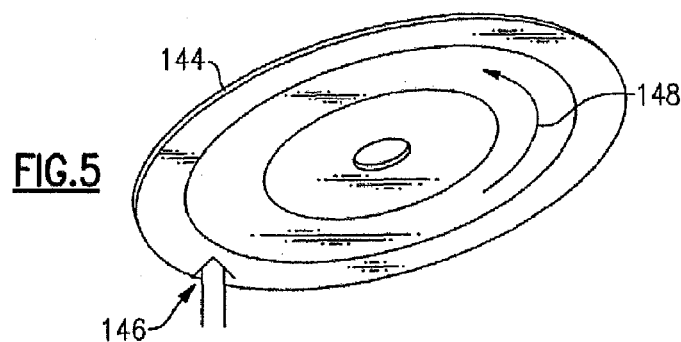
FIG. 5 shows a common arrangement of a reading laser beam relative to a spinning optical disc.

An optical disc spins in a disc reader clockwise when looking down on the disc. From the viewpoint of the reader's laser (looking up), however, the disc is spinning counter-clockwise. FIG. 5 demonstrates a common arrangement of an optical disc in a disc drive. The same arrangement can be employed in the present invention. The laser beam 146 is directed to the optical disc 144 from below. The optical disc 144 spins in a counter-clockwise direction 148 as seen from below the disc. From above the disc, however, the disc 144 spins in a clockwise direction.

The optical disc of the present invention may be designed based on modifications of a standard CD-R disc. The standard CD-R disc is a "forward" disc, in which the operational structure is positioned at the laser-distal surface of the operational layer. Whereas the operational structure of a forward disc is a wobble groove, the disc is also referred to as a "forward wobble" disc. A forward wobble disc has its wobble groove positioned on the second surface or the laser distal surface of the operational layer.

Figure 6:
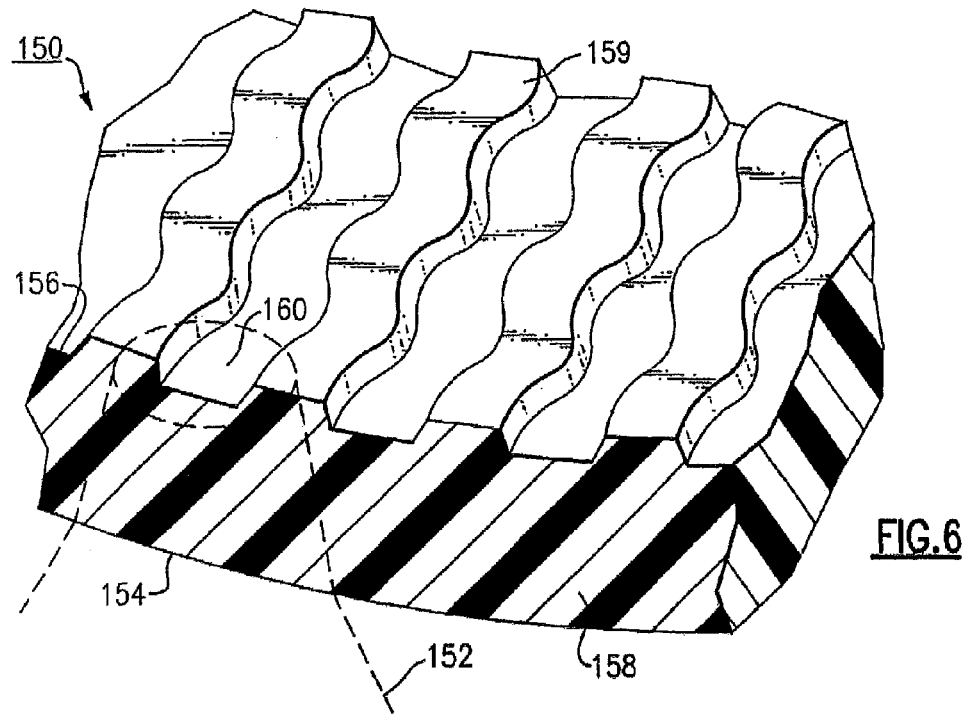
FIG. 6 shows wobbled grooves in a forward wobble optical disc, wherein the wobble grooves are embossed in the laser-distal surface of the operational layer.

FIG. 6 illustrates a forward disc 150. Laser beam 152 enters the operational layer 158 at its first or laser-proximal surface 154. The light is bent according to the refractive property of layer 158. The focus of the laser beam 152 encompasses the bottom of wobble groove 160. Wobble groove 160 is embossed in the second or laser-distal surface 156 of layer 158. Reference numeral 159 denotes a land of the wobble groove.

Figure 7:
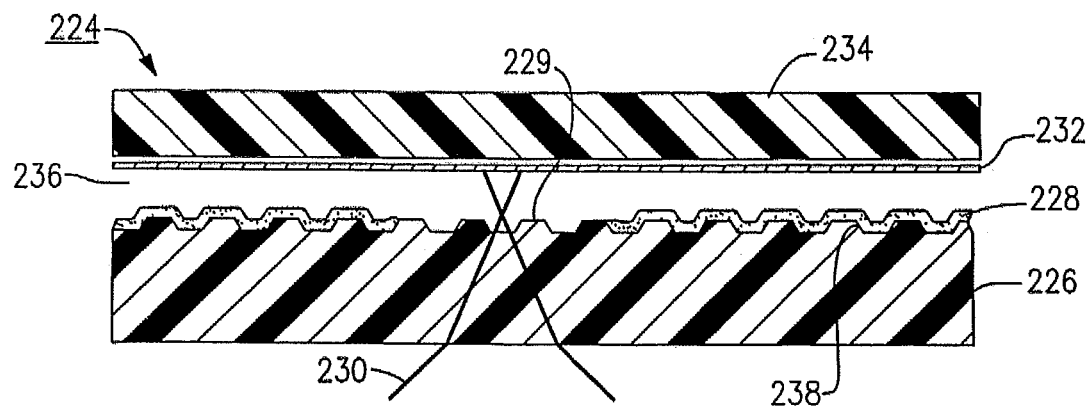
FIG. 7 shows a forward wobble disc assembly containing wobbled grooves coated with a reflective layer, wherein the operational surface has a cut-away area.
Figure 8:
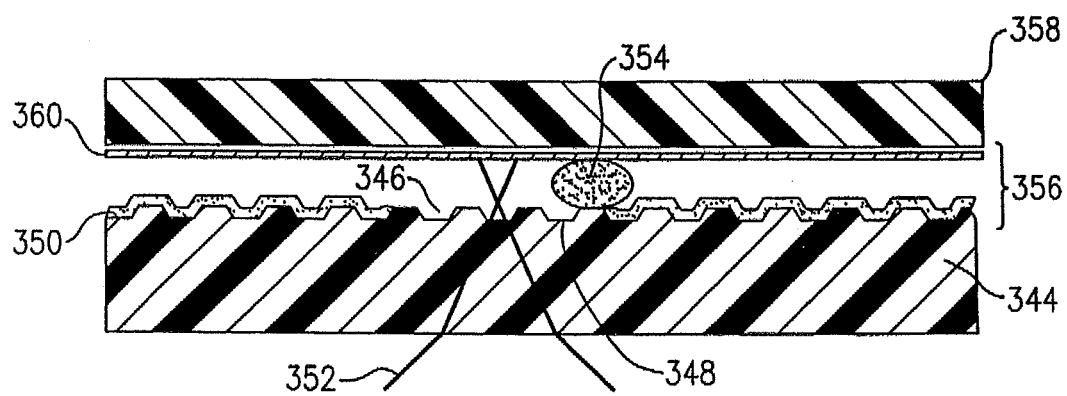
FIG. 8 shows a cross-sectional view of a forward wobble optical disc assembly with an investigational feature placed on a cut-away area.

FIGS. 7 and 8 illustrate the forward discs that may be employed in the present invention. The forward optical disc assembly 224 in FIG. 7 includes an operational layer 226 which has wobble grooves in its laser-distal surface. The wobble grooves are coated with a reflective layer 228 containing reflective material, such as gold. The reflective layer 228 may be semi-reflective. The operational surface has a cutaway area at location 229 which allows laser light 230 to pass through the wobble grooves and reach another reflective layer 232. The reflective layer 232, which contains reflective material, can be deposited on a top cover layer 234 which can provide a stable surface for the reflective layer 232. Assembly 224 also has an analyte section 236 which is configured to receive analytes of interest. The tracking of the disc is performed by the laser beam 230 when it encounters the reflective layer 228 that covers the wobble grooves. The size and configuration of the cut-away portion 229 is calculated to allow the laser to resume tracking before control of the disc is lost by the disc drive's tracking mechanism. The reflective layer 232 permits the laser beam to return to a detector in the disc reader after the laser beam passes through the cut-away portion 229 to the analyte section 236.

As used herein, a "cut-away" area refers to an area in the operational surface, wherein the area either lacks operational structures or the operational structures in the area are changed in certain ways. The operational structures in a cut-away area may be deprived of reflective coatings, or be coated with a reflective material having a different reflectivity than the reflective material coated on other regions in the operational surface. In a preferred embodiment, one surface of the analyte section is adjacent to a cut-away area, or includes a cut-away area.

FIG. 8 shows another forward optical disc which includes an investigational structure 354. The operational layer 344 contains the operational structures which are embossed at its laser-distal surface and coated with a reflective layer 350. The operational layer serves as a lens layer and can focus the laser beam 352 on the operational structures. The analyte section 346 is configured to hold an investigational structure 354, which is within the focal zone 356 of the optical disc reader's laser. The laser beam 352 may pass through a cut-away area 348 and be focused on the investigational structure 354. The cut-away area lacks the reflective coating. The disc assembly has a second reflective layer 360 which is laser-distal to the operational structures and capable of reflecting laser light. The cover 358 is laser-distal to the second reflective layer. The analyte section 346 contains the cut-away area 348 upon which the investigational structure 354 is positioned.

As used herein, a laser's focal zone refers to the range of distance within which the laser's focal point may be positioned. In a standard CD drive, the laser's focal zone is about 25 to 26 micrometers. Thus, the laser's focal point can move above and below a trackable surface in a range of about 12.5 to 13 micrometers. Some variations (about ±2 micrometers) are allowed for the movement. Accordingly, in a preferred embodiment, the analyte section is capable of positioning an analyte at least within about 15 micrometers from the trackable surface in order for the laser reading beam of the optical disc reader to be focused on the analyte. When a hologram is used to encode operational structures, the analyte preferably is located within about 15 micrometers from the image plane of the hologram. In one embodiment, a surface of the analyte section is located within about 15 micrometers from the trackable surface or the image plane of the hologram. The surface of the analyte section may also be capable of receiving the analyte. The surface of the analyte section may be part of a larger surface of the analyte section. The 15 micrometers limitation may be modified in a modified optical disc reader.

In a preferred embodiment, the optical disc assembly employs a spiral wobble groove to provide operational signals. As used herein, a spiral wobble groove can be considered as a series of wobble grooves connected consecutively to form a spiral track. The depth of the wobble groove is preferably from 50 to 100 nanometers, including 65 nanometers, 70 nanometers, 73 nanometers and 100 nanometers. More preferably, the depth of the wobble groove is approximately ⅛ of the effective wavelength of the laser light in the layer which is immediately laser-proximal to the operational surface. Such a depth may provide a strong tracking signal. The groove may also have a depth approximately equal to any odd multiple of ⅛th of the wavelength, such as ⅜ths or ⅝ths. The depth of the groove may remain substantially constant along the wobble groove. The periodic perturbation of the wobble provides the information for tracking. In one embodiment, the spiral groove has a track pitch of approximately 1.6 microns.

Preferably, no dye is laid down in the wobble groove, or the dye is laid down in discrete patterns so as to facilitate drive control during the examination of investigational features. The present invention discovers that a conventional CD-R wobble groove without dye is readable by a standard optical disc reader. The groove can be coated with a layer of reflective material, such as gold, or semi-reflective material. The reflective layer preferably is positioned sufficiently close to the groove structure so as to provide adequate reflection when the laser light focuses on the groove structure. In addition, the pitch and angle of the groove walls can be selected to facilitate the detection of investigational features which are placed on or between various surfaces or layers in the disc.

In accordance with one aspect of the present invention, the optical disc assembly is a "reverse" disc. The operational structures in a reverse disc are imprinted or impressed in the laser-proximal surface of the operational layer. When the operational structure is a wobble groove, the reverse disc may also be referred to as a "reverse wobble" disc. A reverse wobble disc has the wobble groove impressed in the laser proximal surface of the operational layer. A standard CD-R disc has the wobble groove impressed in the laser-distal surface of the operational layer.

Figure 9:
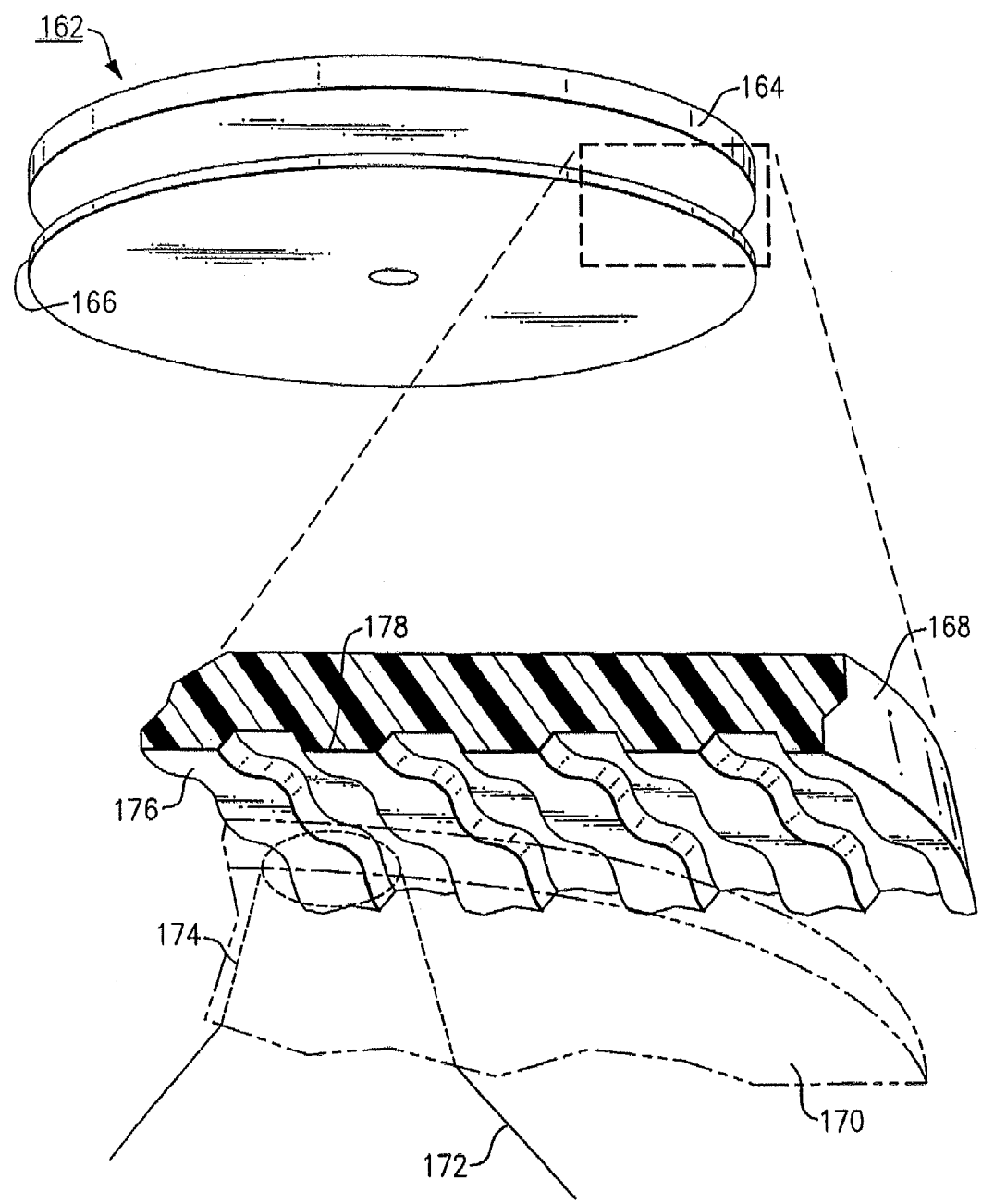
FIG. 9 demonstrates a reverse wobble optical disc assembly, wherein the wobble grooves are embossed in the laser-proximal surface of the operational layer.

FIG. 9 depicts a reverse wobble disc assembly 162. The reverse wobble disc assembly 162 includes an operational layer 164 and a cover 166. The operational layer 164 is further shown in an enlarged view 168. Cover 170 represents the enlarged view of cover 166. Cover 170 provides the most laser-proximal layer in the disc assembly. The laser beam 172 enters cover 170 at its laser-proximal surface 174. The laser beam at surface 174 is bent due to the refractive property of cover 170. The laser exits the cover and is focused on the wobble groove 176 which is embossed in the laser-proximal surface 178 of the operational layer 168. The laser may or may not pass through the wobble groove to reach other layers.

Figure 10:
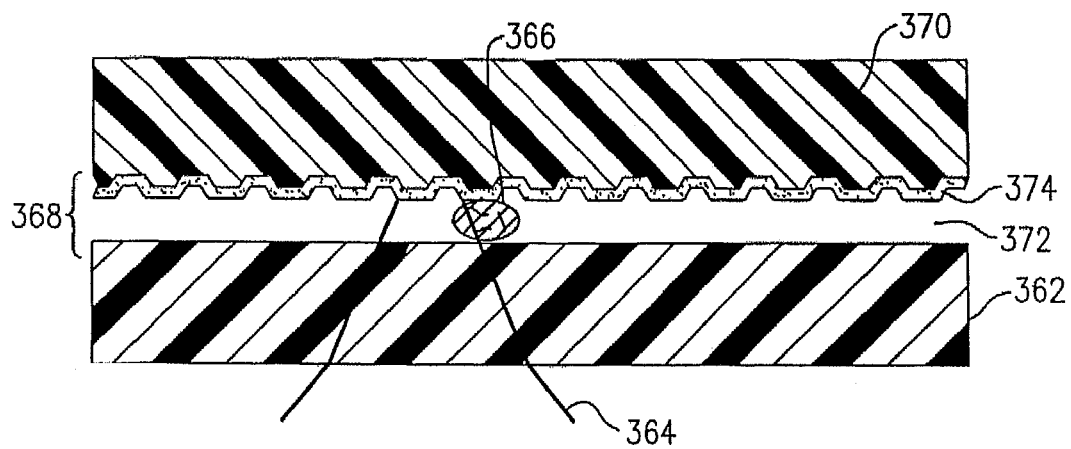
FIG. 10 presents a cross-sectional view of a reverse wobble disc assembly with an investigational feature placed in the analyte section.

FIG. 10 shows a reverse wobble disc containing an investigational structure. The cover 362 acts as a lens to focus the laser beam 364 onto the operational structures. The laser beam 364 may also be focused on the investigational structure 366, depending the reflectivity of the investigational structure 366. The investigational structure 366 is held in the analyte section 372 which is between the operational layer 370 and the cover layer 362. The analyte section 372 lies within the laser's focal zone 368 which also encompasses the operational surface. The operational structures are covered by a reflective layer 374.

Figure 11:
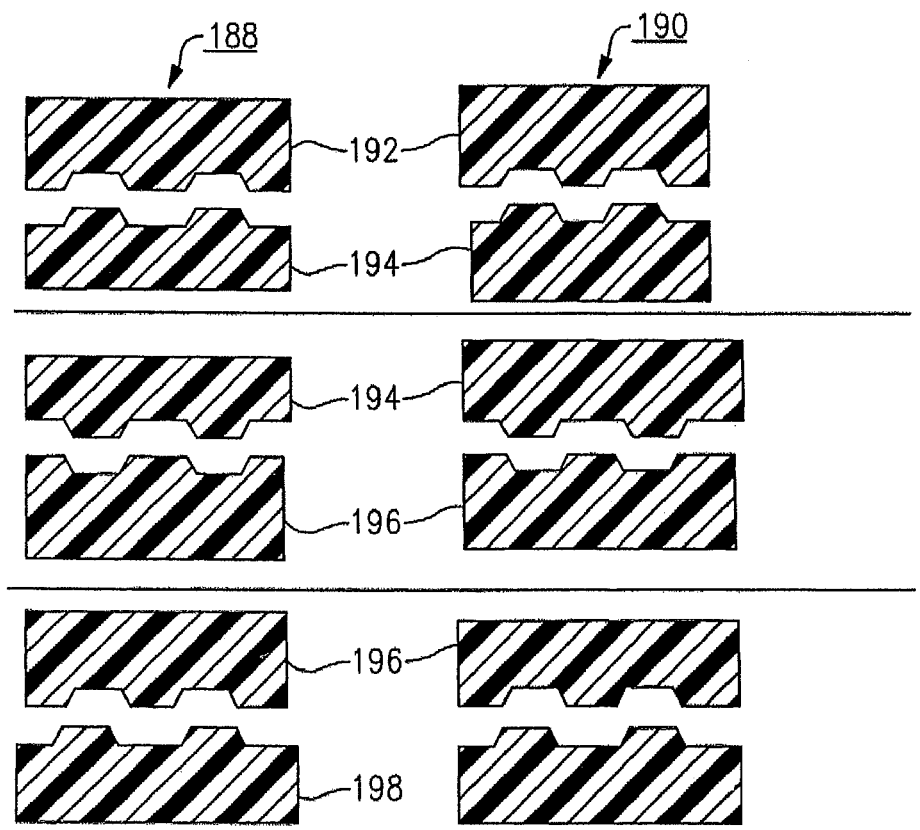
FIG. 11 compares the mastering process for making a forward disc with the mastering process for making a reverse disc.
Figure 12:
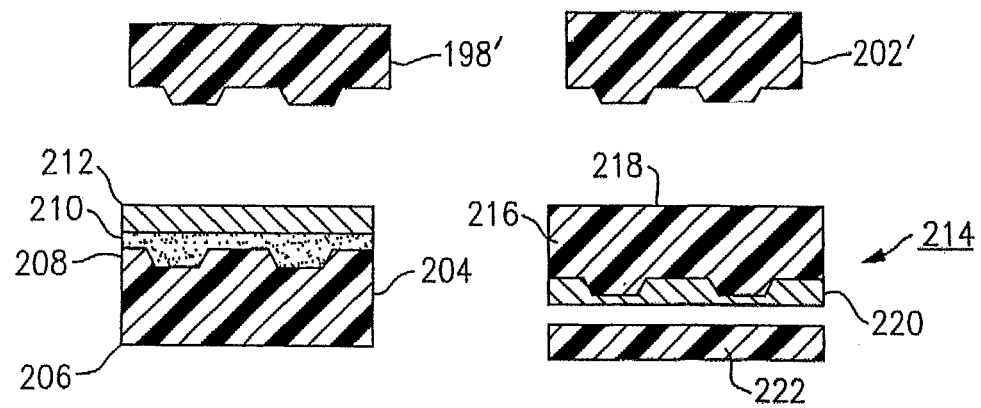
FIG. 12 further compares the mastering process for making a forward disc to the mastering process for making a reverse disc.

The process for manufacturing a reverse wobble disc is different from the process for making an industry standard forward wobble disc. FIGS. 11 and 12 demonstrate the difference between making a reverse wobble disc and making a forward wobble disc. The process for making a normal, forward wobble CD-R is shown at 188, whereas the process for making a reverse wobble disc is shown at 190. In both cases, a master 192 is made. A father stamper 194 is made from master 192, as appreciated by one of skill in the art. A mother 196 is made from the father stamper 194. The image embossed in the mother 196 is thus a duplicate of the original master 192. To make a forward wobble disc, a son stamper 198 is further made from the mother 196. The son stamper 198 has an image identical to that of the father stamper 194. A forward wobble disc, as shown in FIG. 12, is then made from the son stamper 198. In contrast, a reverse wobble disc 202 is made from the mother stamper.

FIG. 12 further illustrates the difference between manufacturing a forward wobble disc and manufacturing a reverse wobble disc. The son stamper 198' is identical to the son stamper 198 in FIG. 11. The son stamper 198' is used to create a wobble groove on the laser-distal surface 208 of the substrate layer 204, therefore creating a forward wobble disc. Surface 208 may be coated with a dye layer 210 which is further layered with a reflective coating 212. Preferably, the surface 208 is directly coated with the reflective coating 212 without the dye layer 210. The laser beam of the disc reader can travel through the most laser-proximal surface 206 and then the operational layer 204 to reach the surface 208. The surface 208 is the operational surface.

In comparison, the reverse wobble discs 214 and 202' are made from the mother stamper. The wobble groove in the reverse wobble disc 214 is positioned at the first or laser-proximal surface of the operational layer 216. Surface 218 is the second or laser-distal surface of the operational layer 216. The cover 222 is capable of focusing the laser beam on the wobble groove. To facilitate the reading of the wobble groove, a reflective layer 220 is deposited on the first surface of layer 216. The first surface of layer 216 is the operational surface. As viewed from the optical pick of the optical disc reader, the operational surface of the reverse wobble disc 214 appears to have the same image as the operational surface 208 of the forward wobble disc.

A reverse wobble disc can be manufactured so that the spiral of the wobble groove moves from the inner diameter of the disc to the outer diameter of the disc when the disc is spun counter-clockwise as viewed from the laser. This configuration is the same as used by a conventional forward wobble disc.

In another embodiment, a reverse wobble disc can be prepared using a process similar to process 190 in FIG. 11. However, the wobble groove in the master disc has a reverse image of the wobble groove in the master disc 192. The reverse wobble disc thus prepared has the wobble groove impressed at the laser-proximal surface of its operational layer. A standard CD-R or CD-RW reader can track both the reverse wobble disc of this embodiment and the reverse wobble disc manufactured using the master disc 192. The disc tracking is dependent upon the frequency of the wobble. Likewise, a forward wobble disc can be created using process 188 but with a master disc having a reverse image of the master disc 192.

Figure 13:
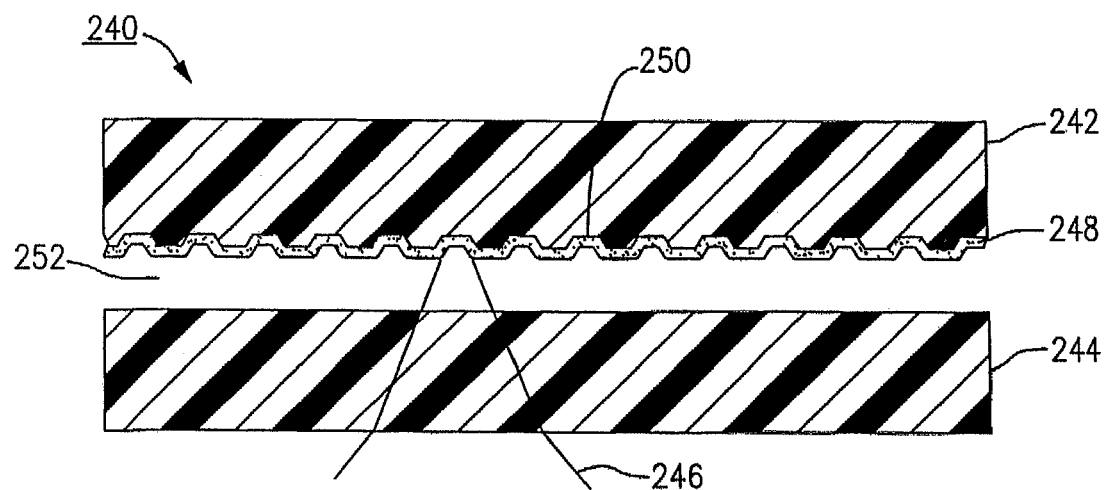
FIG. 13 illustrates a reverse optical disc assembly.

FIG. 13 demonstrates a reverse disc according to one embodiment of the present invention. The reverse disc 240 includes an operational layer 242 which contains a wobble groove 250 at its laser-proximal surface. The wobble groove 250 is coated with a reflective layer 248 which contains reflective material, such as gold. The laser beam 246 can be focused by the cover 244 upon the wobble grove 250 or upon the reflective layer 248. The assembly 240 permits investigational structures to be placed in the analyte section 252 and to be examined by the laser beam 246.

For more information about optical discs in which operational structures are positioned in the laser-proximal surface of the operational layer, see U.S. patent application Ser. No. 09/421,870, entitled "Trackable Optical Discs With Concurrently Readable Analyte Material," which is incorporated herein by reference.

In accordance with one aspect of the present invention, various types of data or information can be digitally encoded in the disc assembly. These data or information may be encoded in accordance with industry standards, such as CD or DVD standards, or standards modified therefrom. These encoded data or information may control or facilitate an optical disc reader to track the disc assembly or detect investigational structures that are disposed in the disc assembly.

Investigational structures that are disposed in an optical disc assembly can be read or detected using an optical disc reader, such as a CD reader or a DVD reader. As used herein, CD readers include, but are not limited to, CD-ROM readers, CD Recordable (CD-R) readers, CD-Rewriteable (CD-RW) readers, or any reader capable of reading CD-format discs. Industry standard CD readers may be used in the present invention. Preferably, a standard CD-RW reader or a modification thereof is used in the present invention. As used herein, DVD readers include, but are not limited to, DVD-R readers, DVD-RAM readers, DVD-RW readers, or any reader that can read DVD-format discs. Industry standard DVD readers may be used. As appreciated by one of skill in the art, other CD readers, DVD readers or optical disc readers, including those that have been or will be developed in the future, may be used in the present invention. An optical disc reader may read both CD and DVD discs.

Signals indicative of the presence or other properties of an investigational structure can be generated by an optical disc reader. The disc reader directs a reading beam of electromagnetic radiation, typically a laser beam, to the optical disc assembly in which the investigational structure is disposed. The disc reader can scan the beam over the area in which the investigational structure is held. The scanning beam can be either reflected from or transmitted through the disc assembly. The reflected or transmitted radiation may be acquired by a detector in the disc reader. Radiation thus acquired can be used to produce signals indicative of the presence or other properties of the investigational structure. Different types of lasers with different wavelengths may be used in the present invention. Whereas a standard optical disc reader is used, the disc reader may be connected to circuitry for processing the signals indicative of the presence or other properties of the investigational structure.

Radiation acquired by the detector of the optical disc reader can also be used to generate operational signals, such as focusing servo signals, tracking servo signals, synchronization signals, power control signals, and logic signals. The focusing servo signals can be generated from at least three focusing techniques: critical angle focusing, knife edge focusing and preferably, astigmatic focusing. Tracking servo signals can be generated from at least four types of tracking techniques: one beam-push-pull tracking, three beam outrigger tracking, differential phase detection tracking, and one beam high frequency wobble tracking. Synchronization signals may be generated from at least three different methods: bit clock synchronization or bit pattern synchronization, zoned clocking method, and wobbling groove synchronization. Logic signals can be produced from various optical disc formats. Logic signals can be used to perform position sensing, power control, radial and tangential location, layer sensing, density detection, or other functions.

Figure 14:
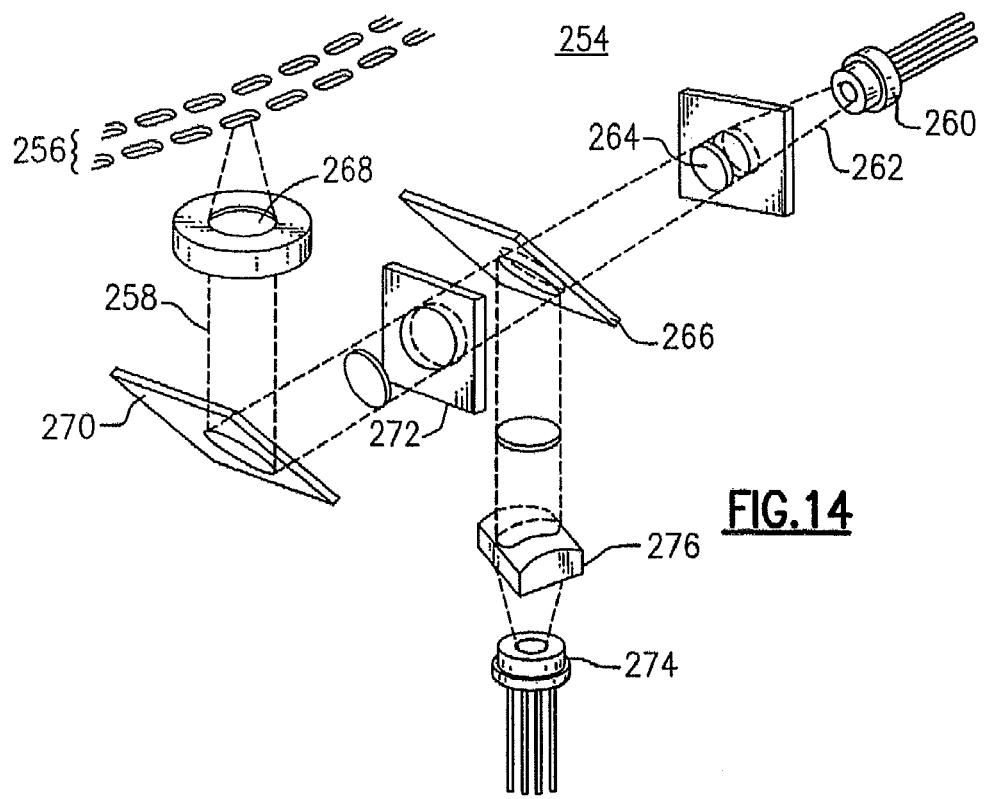
FIG. 14 illustrates an optical pickup used in one embodiment of the present invention.

Preferably, the optical pickup of a standard CD reader is used to both track the optical disc assembly and detect the investigational structure disposed therein. FIG. 14 illustrates an example of the optical pickup of a standard CD reader. The optical pickup 254 contains a laser source 260, which typically is a laser diode. The laser source emits a laser beam 262. The laser beam is collimated by a collimator lens 264. The collimated beam is then directed toward the optical disc through a polarization beam splitter 266. The objective lens 268 focuses the laser beam onto a small spot on a surface in the optical disc. In FIG. 14, the surface is the operational surface of a CD-type optical disc, which contains pits and lands 256. The surface preferably is coated with a reflective layer, so that the laser beam can be reflected therefrom and then directed by the objective lens 268, the mirror 270 and the quarter wave plate 272 to the beam splitter 266. As the light is now polarized in a different direction as compared to the source polarization, it can be directed by the beam splitter towards a photodiode detector 274. A cylindrical lens 276 may serve as an astigmatic element to introduce astigmatism in the reflected laser beam for the purpose of focusing.

Figure 15:
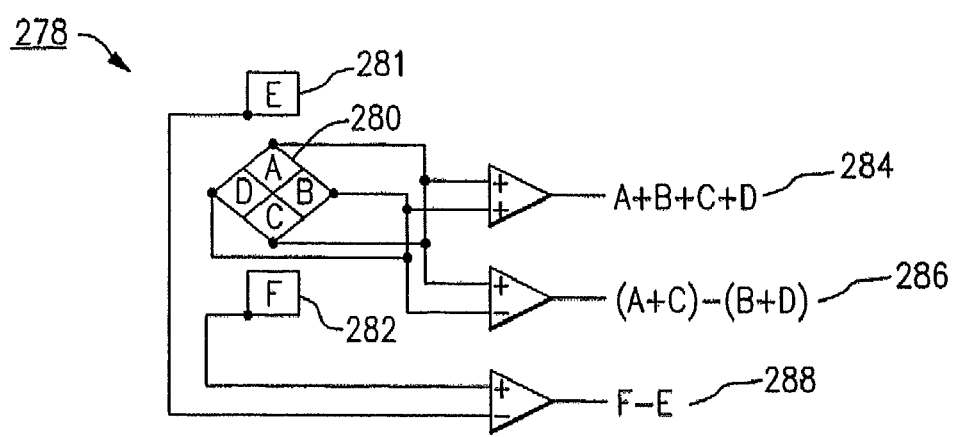
FIG. 15 depicts a quad detector used in one embodiment of the present invention.

In a preferred embodiment, the laser beam is split into three beams, consisting of a main beam and two tracking beams, and the detector is a quad detector. FIG. 15 shows a quad detector 278, which includes a central quad detector 280 flanked by two additional sensor elements E 281 and F 282. The main beam is centered on a track defined by pits in a CD-ROM disc. The tracking beams fall on either side of the track. By design, the three beams are reflected from the optical disc and then directed to the quad detector 278 such that the main beam falls on the central quad detector 280, which includes sensor elements A, B, C, and D, while the tracking beams fall on the sensor elements E 281 and F 282. The sum of the signals from the central quad detector, i.e. A+B+C+D, provides the radio frequency (RF) signal 284, also referred to as the high frequency (HF) or the quad-sum signal. A tracking error signal (TE signal) 288 may be obtained from the difference between E and F. Because astigmatism is introduced by the cylindrical lens astigmatic element, a focus error signal (FE signal) 286 may be obtained from the difference between A+C and B+D signals. Other combinations of the signals from A through F may be obtainable, as appreciated by one of ordinary skill in the art. These combinations of signals may be used to track the disc and read the investigational structure disposed in the disc. A quad detector and a similar optical design may be employed in a DVD reader.

In one embodiment, the quad-sum signal is used for extracting information indicative of the presence or other properties of the investigational structure disposed in the disc assembly. Preferably, the disc assembly contains a wobble groove which is trackable by a disc reader. Suitable disc readers include CD-R readers, CD-RW readers or DVD readers. The use of the wobble groove enables the segregation of the tracking signal from the quad sum signal, permitting the quad sum signal to be used to detect signals from investigational structures. If the investigational structure is small enough, an electrical deflection may be detected in the quad-sum signal, while no such a deflection, or a comparatively smaller electrical impulse, will be noted in the tracking signal or the focusing servo signal.

Figure 31:
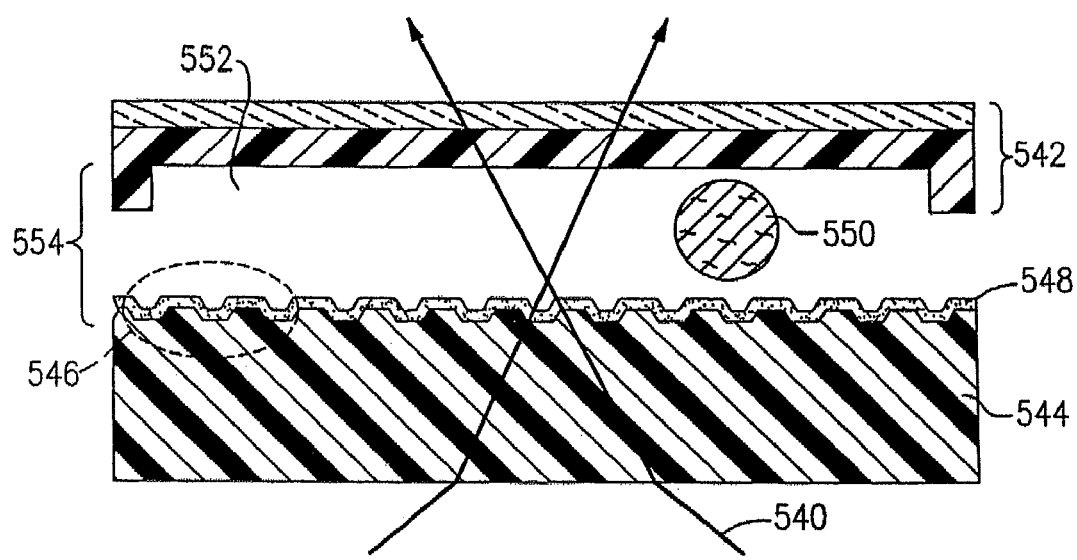
FIG. 31 shows a example of a forward disc which permits the laser light to pass through the disc to a top detector.
Figure 37:
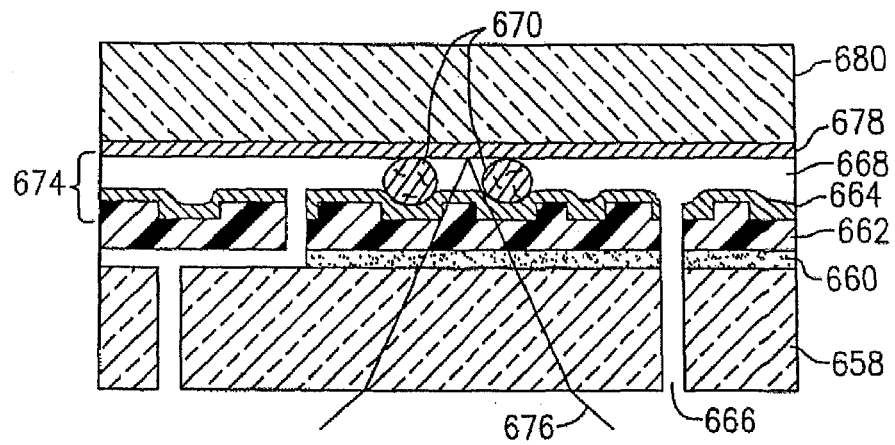
FIG. 37 shows a forward optical disc assembly, wherein channels are contained in a lens layer.

A large investigational feature may also be detected by using the quad-sum signal without losing the tracking of the disc assembly. In such a case, a forward disc, such as that shown in FIGS. 31 and 37, is preferably used. The ability of an operational structure, such as the wobble groove, to permit both disc tracking and analyte detection is herein referred to as segregation of tracking from investigational structures.

The signals produced from a wobble groove can be used by the disc reader to maintain a constant linear scanning velocity at all points on the disc. This allows determination of the dimensional information of the investigational structure that is placed in the disc. Therefore, wobble groove is a preferred operational structure employed in this invention.

Although the above-described embodiment uses the quad-sum signal and the wobble groove, signals other than the quad-sum signal and operational structures other than the wobble groove may be used for the detection of investigational structures. For instance, the focus error signal obtained by the critical angle method, as described in U.S. Pat. No. 5,629,514, may be used. The Foucault and astigmatism methods, as described in "The Compact Disc Handbook," by Pohlmann, A-R Editions, Inc. (1992), may also be employed. In addition, the tracking error signals obtained using the single beam push-pull method as described in "The Compact Disc Handbook," by Pohlmann, A-R Editions, Inc. (1992), the differential phase method as described in U.S. Pat. No. 5,130,963, or the single beam high frequency wobble method can be used for the present invention. The block error rate information, such as those used by a CD reader to reduce the effect of scratches on a CD surface, or the movement of the focusing servo may be used.

For more optical pickup designs and operational signals that may be used in the present invention, see "Compact Disc Technology," by Nakajima and Ogawa, IOS Press, Inc. (1992); "The Compact Disc Handbook," by Pohlmann, A-R Editions, Inc. (1992); "Digital Audio and Compact Disc Technology," by Baert et al. (eds.), Books Britain (1995); "CD-Rom Professional's CD-Recordable Handbook: The Complete Guide to Practical Desktop CD," Starrett et al. (eds.), ISBN:0910965188 (1996). All these references are incorporated herein in their entirety by reference.

U.S. Provisional Application Ser. Nos. 60/270,095 and 60/292,108 further detail how to extract or process signals indicative of the presence of an investigational structure disposed in an optical disc assembly. Both applications are incorporated herein by reference.

Figure 16:
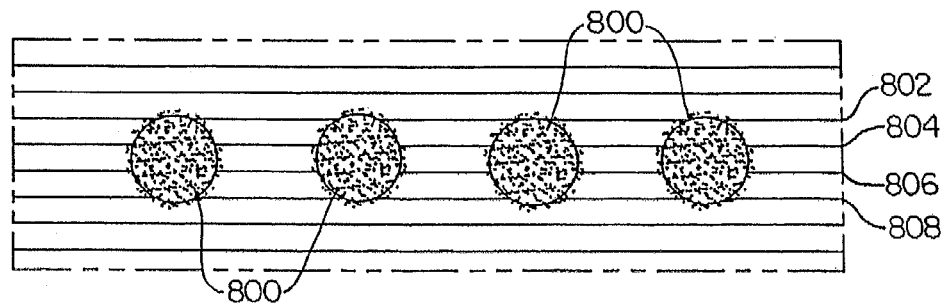
FIG. 16 depicts the positions of investigational structures with respect to the tracks of operational structures.
Figure 17:
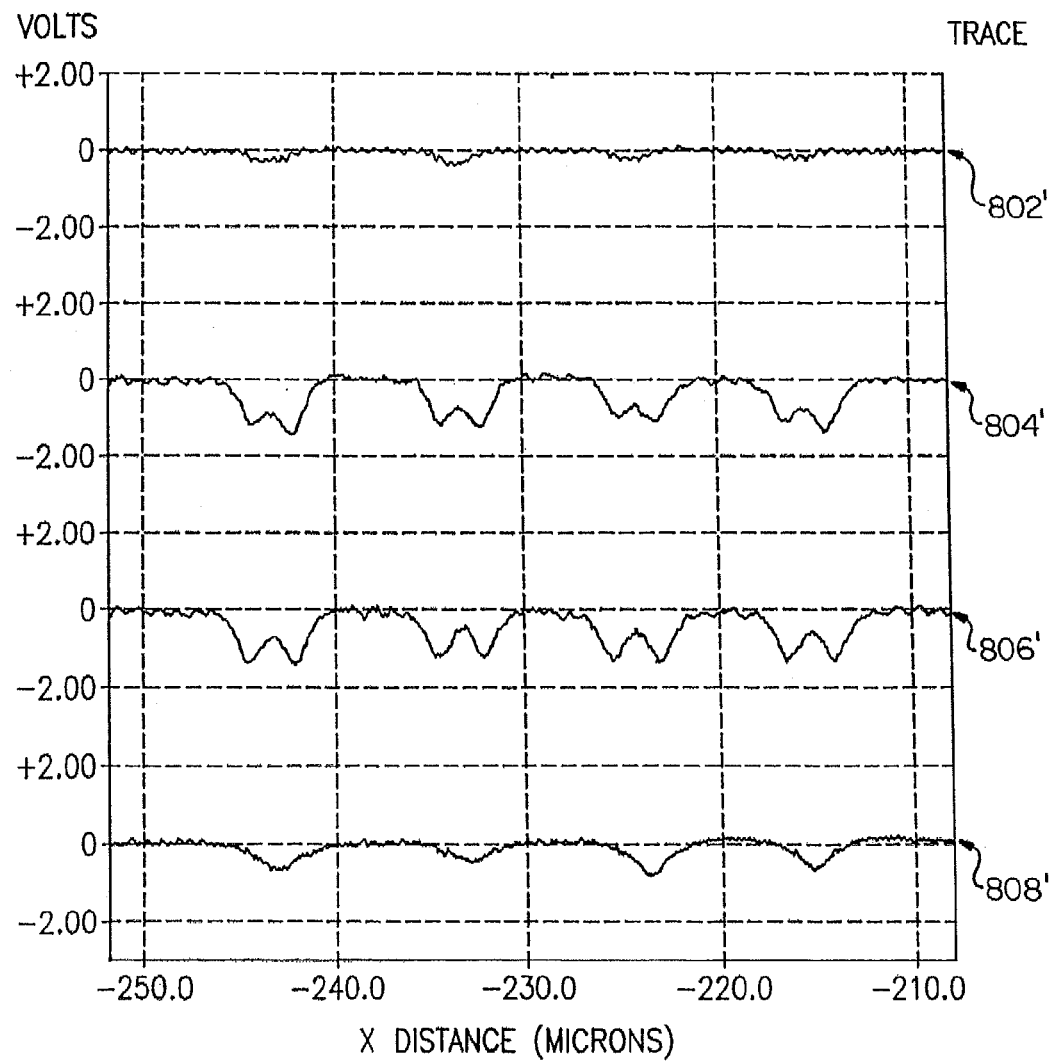
FIG. 17 shows the HF signals acquired from the tracks illustrated in FIG. 16.

FIG. 16 and FIG. 17 illustrate a measurement of investigational structures using an optical disc assembly according to one embodiment of the present invention. The analyte section is laser-proximal to the operational layer, and is positioned between the operational surface and a lens layer. FIG. 16 depicts the position of the investigational structures 800 with respect to the tracks 802, 804, 806 and 808. The investigational structures 800 are held in the analyte section and positioned on the operational surface. The investigational structures 800 are 2.8 micrometer magnetic beads. Tracks 802, 804, 806 and 808 are embossed in the operational surface. Each track preferably is in the form of a wobble groove.

FIG. 17 shows the HF signals 802', 804', 806' and 808' that are acquired along the tracks 802, 804, 806 and 808, respectively. The HF signals shown in FIG. 17 have been digitalized and buffered. The HF signals 802', 804', 806' and 808' demonstrate the existence as well as the approximate dimension of the investigational structures 800.

Figure 18:
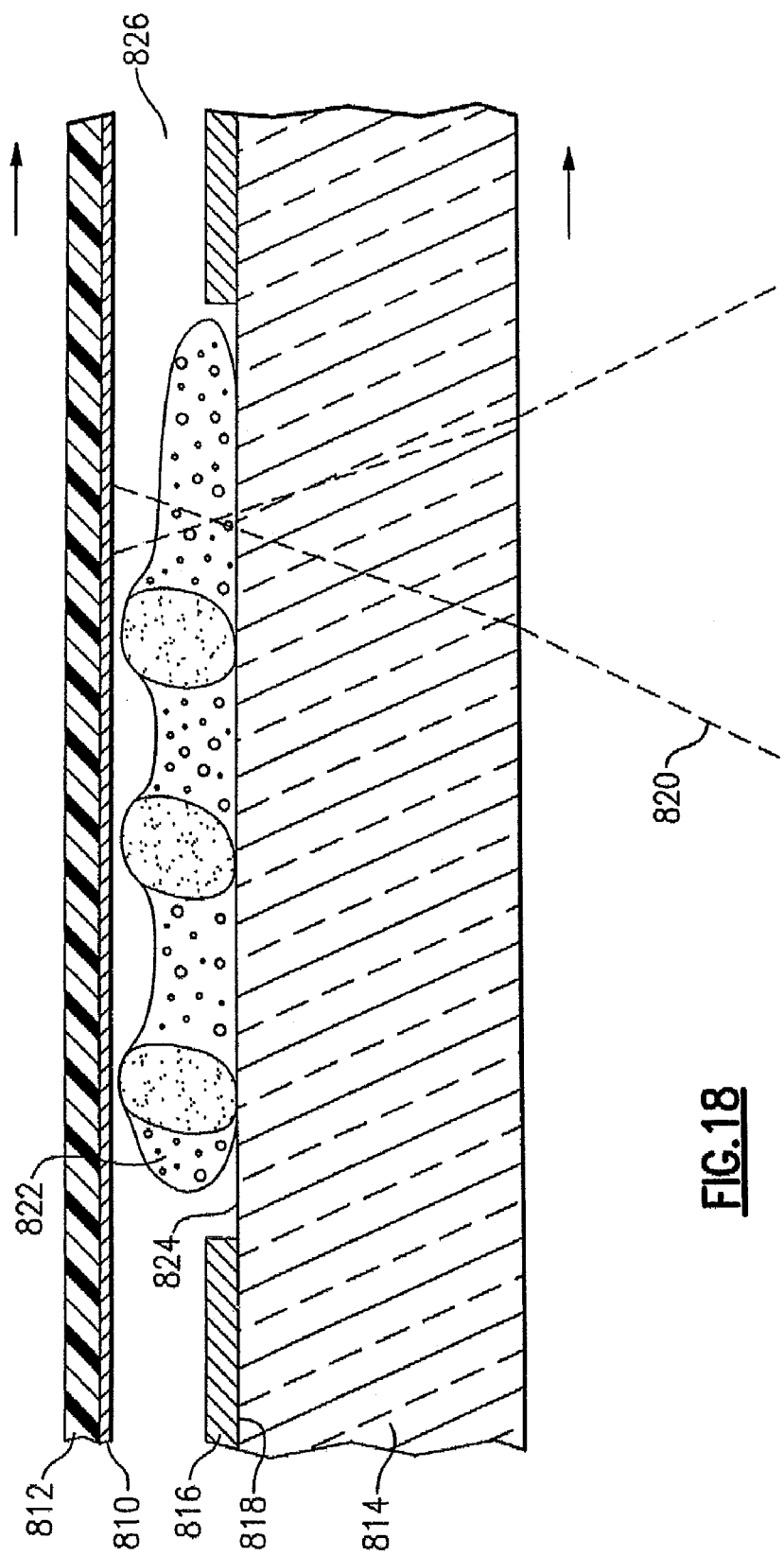
FIG. 18 shows an optical disc assembly including a gnat wing in an inspection channel.

FIGS. 18 through 24 illustrate the measurement of a gnat wing disposed in an optical disc assembly. FIG. 18 is a cross-sectional view taken perpendicular to a radius of the optical disc assembly. In FIG. 18, the optical disc assembly includes an operational layer 814, a first reflective layer 816, a second reflective layer 810 and a cover 812. The analyte section 826 is located between the second reflective layer 810 and the operational layer 814. The operational surface 818 is the laser-distal surface of the operational layer 814. The operational surface 818 is embossed with tracks of operational structures, preferably, wobble grooves. The operational surface 818 is covered by the reflective layer 816. The operational surface has a cut-away area 824 which may lack the reflective coating 816. The gnat wing 822 is located in the analyte section 826 and positioned upon the cut-away area 824. The laser beam 820 can pass through the operational layer 814, the cut-away area 824 and the gnat wing 822, and then be reflected by the reflective layer 810.

Figure 19:
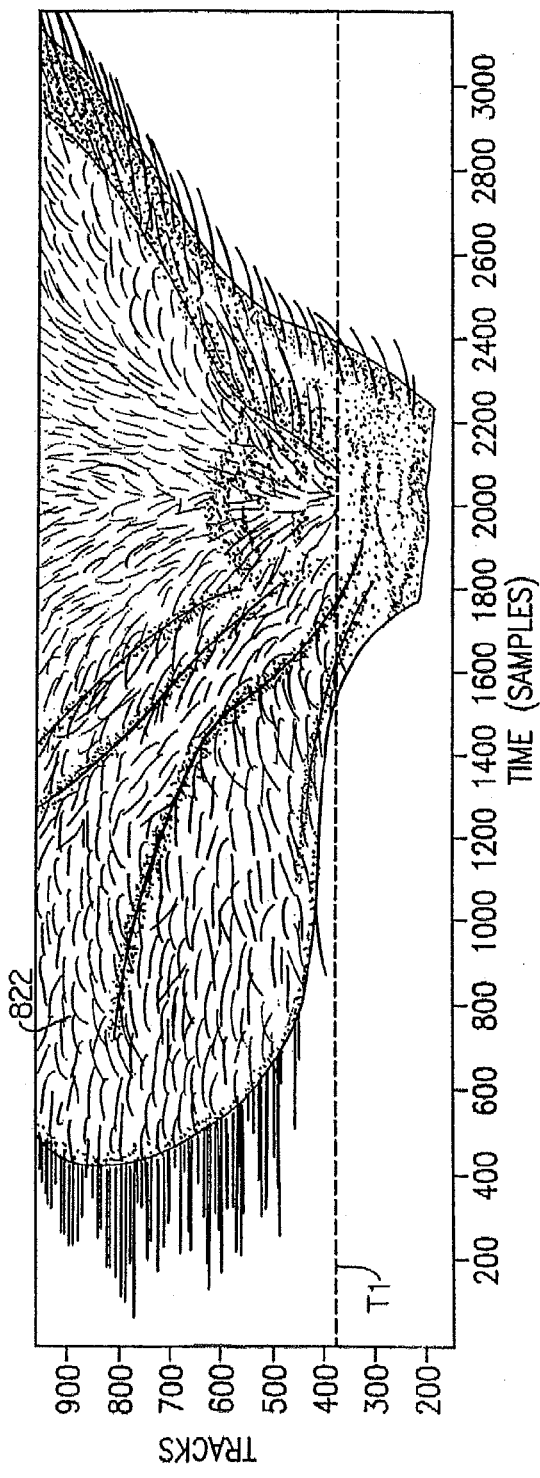
FIG. 19 depicts the position of the gnat wing with respect to the tracks of the operational structures.
Figure 20:
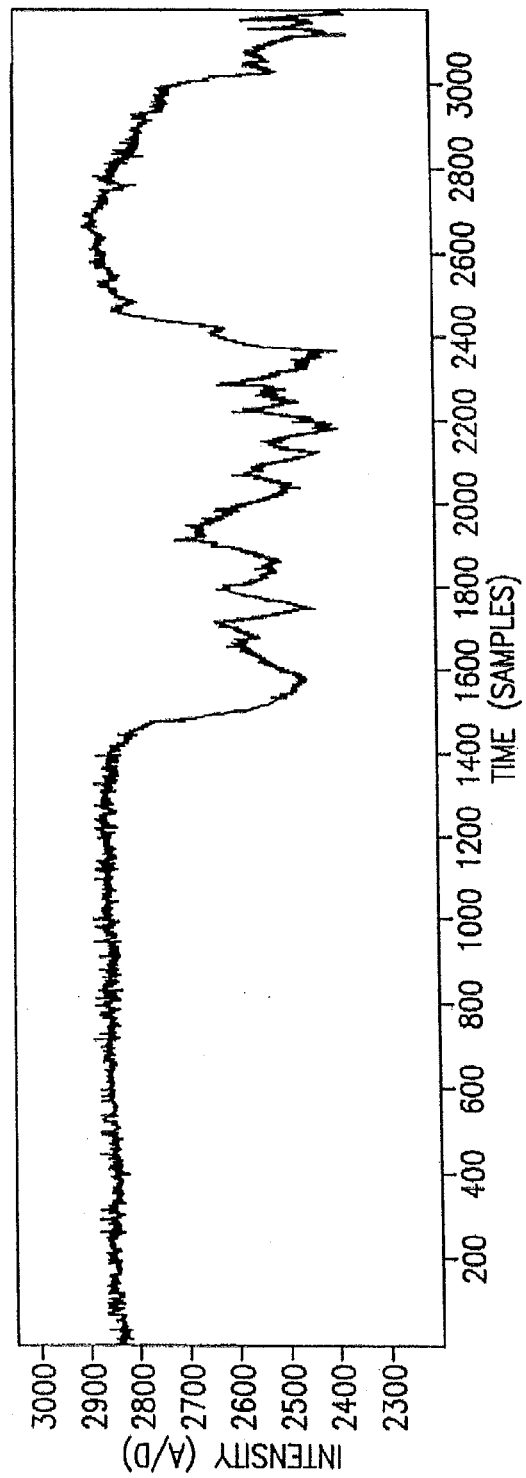
FIG. 20 shows the HF signals acquired from a track of the operational structures illustrated in FIG. 19.

FIG. 19 diagrammatically shows the position of the gnat wing 822 relative to the tracks embossed in the operational surface. T1 denotes a track upon which the gnat wing is positioned. FIG. 20 shows the HF signal acquired along the track T1. The HF signal has been digitalized and buffered.

In FIG. 19, the Y-axis, labeled with "TRACKS," represents the number of tracks along a radius of the disc assembly. The X-axis, labeled with "TIME (SAMPLES)," represents the number of sampling along a track. For instance, the gnat wing can be sampled by the disc reader along the track T1 at least about 800 times (from sample number 1550 to sample number 2350).

Figure 21:
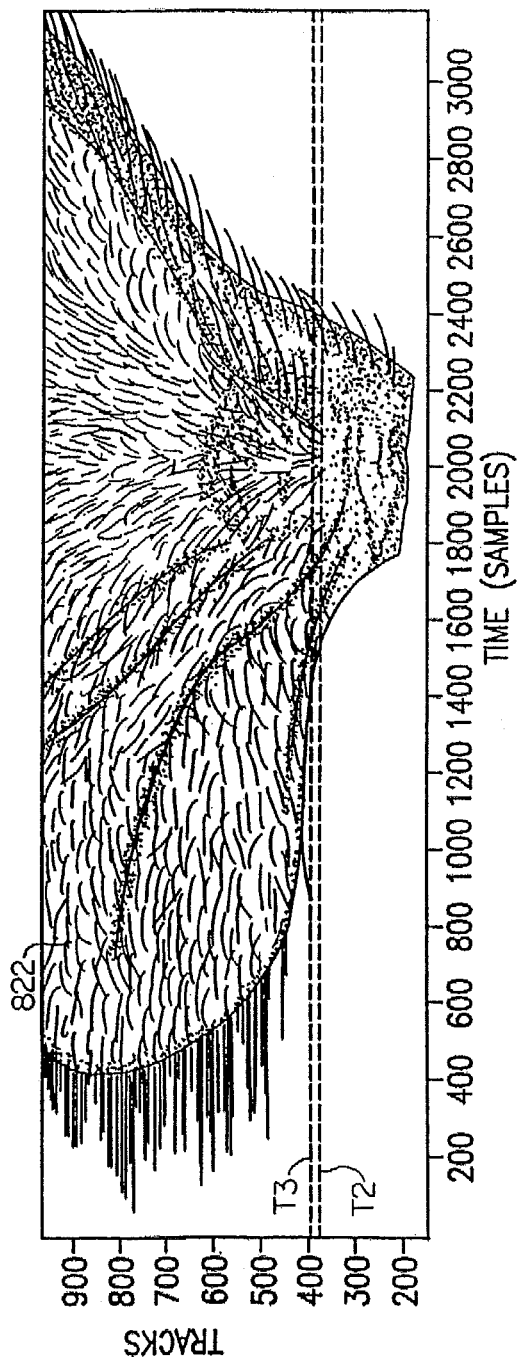
FIG. 21 depicts the position of the gnat wing with respect to the tracks of the operational structures.
Figure 22:
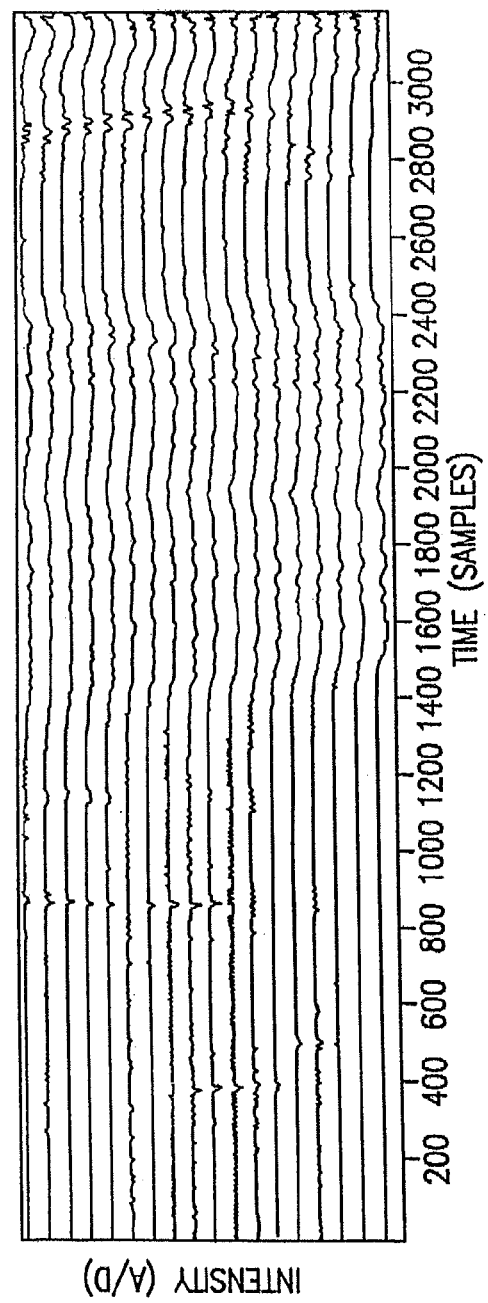
FIG. 22 demonstrates the HF signals acquired from a series of consecutive tracks of the operational structures illustrated in FIG. 21.

FIG. 21 shows the position of the gnat wing 822 relative to the tracks T2 and T3. FIG. 22 demonstrates the HF signals for a series of consecutive tracks between T2 and T3.

Figure 23:
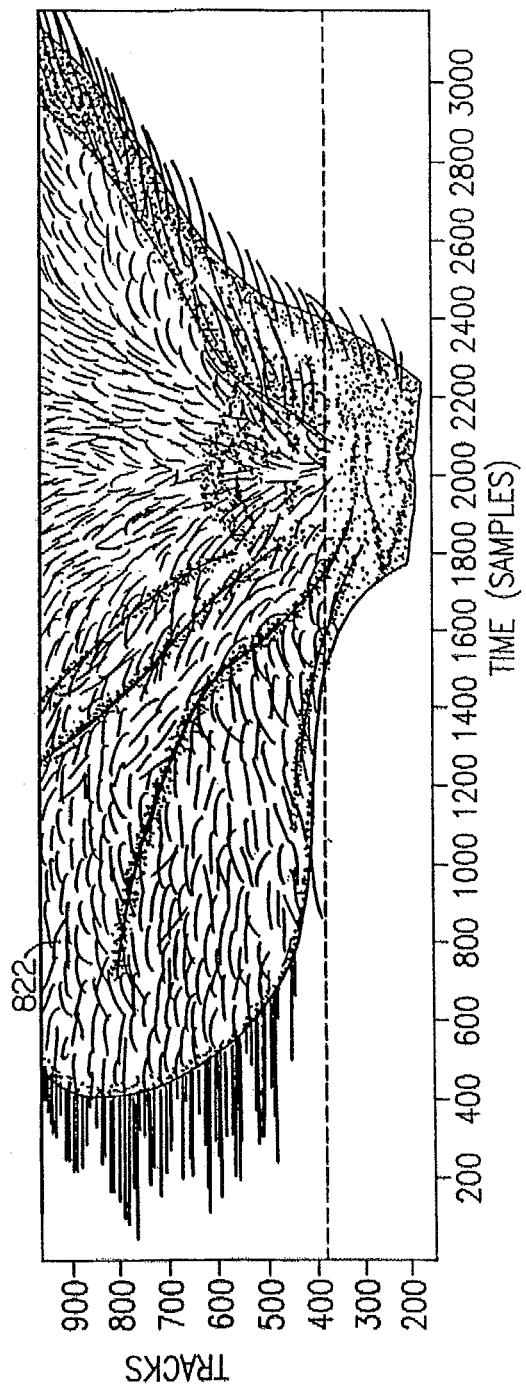
FIG. 23 depicts the position of the gnat wing with respect to the tracks of the operational structures.
Figure 24:
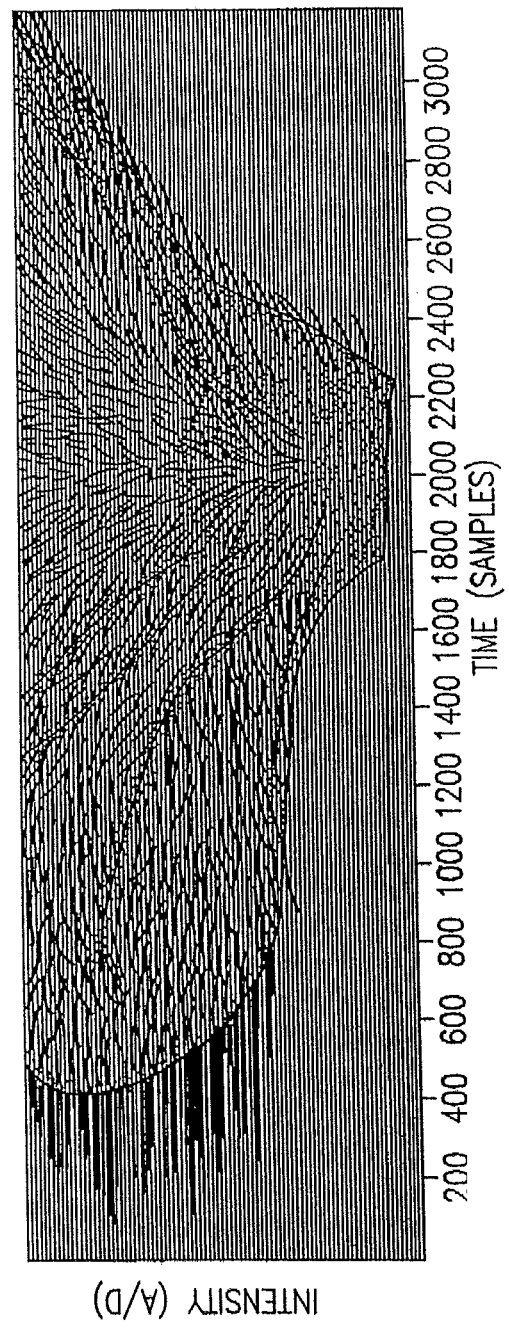
FIG. 24 shows a high density compilation of the HF signals acquired from the tracks across the gnat wing.

FIG. 24 is a high density compilation of the HF signals for the tracks across the gnat wing. The image of the gnat wing appears in FIG. 24. FIG. 23 shows the position of the gnat wing 822 relative to the tracks.

Figure 25:
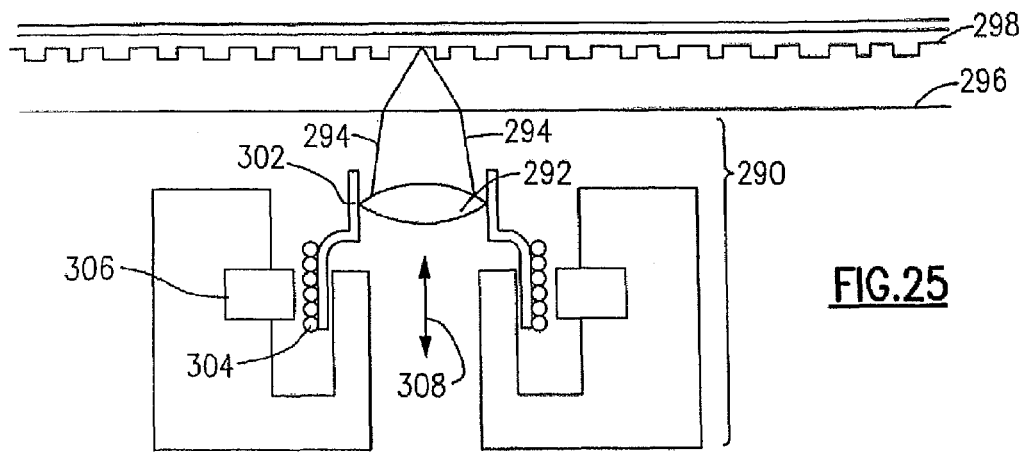
FIG. 25 shows an objective lens focusing mechanism as used in one embodiment of the present invention.

In accordance with another aspect of the present invention, the optical disc reader includes an objective lens focusing mechanism which is capable of focusing the disc reader's laser onto different surfaces in the disc assembly. In one embodiment, the focusing servo 290 shown in FIG. 25 includes a coil and magnet casing surrounding the objective lens. The objective lens 292 directs the laser 294 onto the surface 296 of the disc. Then the laser light travels through a lens layer, and focuses onto the operational surface 298.

The operational surface contains operational structures, such as wobble grooves, or pits and lands. The objective lens is held by a brace 302 which is part of the moving coil controlled by the magnet 306. The magnet 306 is activated by the signal generated when the laser light 294 returns from the disc to the detector of the disc reader. The moving coil 304 and the objective lens can move within the range 308. The range 308 controls the range of the laser's focal zone.

The focusing servo of the present invention may move the laser's focal point across the laser's focal zone. The laser's focal point may represent the point where the focusing servo finds a maximal amount of light returned to the disc reader's detector. The location of the laser's focal point therefore may be affected by the reflective properties and other optical properties of various elements contained in the optical disc assembly. For instance, where the optical disc assembly is based on the modification of a conventional CD-R, the focal point may be at the reflective layer which contains gold or other reflective material.

More than one reflective layer, including semi-reflective layers, may be constructed within the laser's focal zone. The reflective layers in the focal zone can create a level of signals, the voltage of which is affected by the position of the focal point and the reflectivity of the reflective layers. The focusing servo may be able to search for a focal point from which the light returned to the detector is maximal.

In a preferred embodiment, the operational structures in the optical disc assembly are designed to provide an improved detection for the investigational structures. The investigational structures may be cells, microorganisms or any other biological, biochemical, or chemical specimens. In one instance, the pits, lands, or wobble grooves are reconfigured to enhance tangential resolution. In another case, the pits are shortened or the wobble is changed to provide a lower scanning speed in order to increase the radial resolution. In yet another instance, the lens layer is changed to PMMA or other material to improve optical response. The lens layer may also be made thicker or thinner to make the focal spot smaller or larger, therefore providing higher or lower energy distributions on the detector. The operational structures may be interleaved to provide dynamic responses for enhancing imaging.

The present invention contemplates a variety of embodiments of the optical disc assembly. For instance, the optical disc can be a forward disc or a reverse disc. The optical disc can have more than two reflective layers. The operational structures can include pits, lands, grooves, wobble grooves, dye marks, chevron marks, or any combination thereof. The operational structures may act as phase components or create interference patterns that provide tracking and synchronization information to the disc drive. The operational structures can be in a CD format (including a CD-R and CD-RW format), a DVD format (including a DVD-R format, a DVD-RW format and a DVD-RAM format), any combination thereof, or any other optical disc format. The operational structures can be physically imprinted in a surface of the operational layer, or encoded in a hologram. A custom format for operational structures may also be used, and the disc assembly is read by a custom decoding device. Different surfaces in the optical disc assembly can be metalized or coated with materials with a variety of reflective properties. The coatings may be reflective, semi-reflective, transmissive, semi-transmissive, or anti-reflective. The materials used in the various layers may be dielectric or non-dielectric. Moreover, the operational layer may be created using different processes, such as molding, electroforming, or web manufacturing.

The analyte section of the optical disc assembly can be configured to receive an insert which holds the analyte of interest. The insert can be glass or plastic. The insert may be a sample slide regularly used for examining biological, biochemical, or chemical samples. The insert may be replaceable or integrated with the disc assembly. The insert may hold chemical, biological or other physical specimens. Chemical or biological reactions, including molecule-molecule bindings or enzymatic reactions, can be performed either on the insert or in the analyte section. Products of these chemical or biological reactions may generate optical effects on the incident laser light which can in turn be detected by the disc reader. The insert may function as a cover layer or a lens layer.

The analyte section may include investigational structures which are replaceable or integrated with the disc assembly. The investigational structures may contain light absorbing, light reflecting materials, or anti-reflective materials, so that they may be detectable by the optical pickup of the disc reader. The focusing servo may search for the focal point with maximal return light. Such a focal point may depend on the reflectivity of the investigational structures.

The analyte section or any other layer in the disc assembly may contain channels or chambers, including microfluidic channels, through which analytes, investigational features or reactive components may enter or exit the analyte section. These channels or chambers may also be used to hold the analytes or investigational features for investigation.

The optical disc assembly of the present invention preferably includes a lens layer. The thickness of the lens layer may be about 1.1 mm to 1.3 mm, including about 1.2 mm. Such a lens layer may be used in a disc assembly that is modified from a CD-type disc. The thickness of the lens layer may also be about 0.6 mm, and can be used in a disc assembly modified from a DVD-type disc. The refractive index of the lens layer preferably is selected so that the laser of the disc reader can be focused in a desired manner. The lens layer may be made from a variety of materials, including glass, plastic, PMMA, polystyrene, polycarbonate, or dyed material. The lens layer may be flat or non-flat. The lens layer may be homogeneous or non-homogenous. The lens layer may be incorporated into the operational layer. The lens layer may contain at least part of the analyte section.

The lens layer may also contain molded features, such as cavities, channels or waveguides. The lens layer may function as a cover to protect the operational layer or other layers of the disc assembly. The lens layer may provide physical support for other layers in the disc or for the investigational structures or the analytes that are associated with the disc. The lens layer may be either laser-proximal or laser-distal to a reflective layer or a semi-reflective layer.

Figure 26:
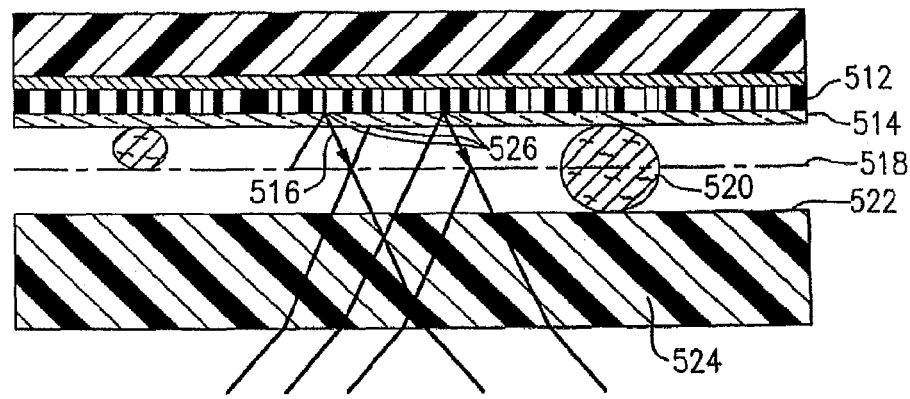
FIG. 26 illustrates an optical disc assembly containing a reflective hologram.

In a preferred embodiment, the operational layer includes or consists of a hologram. The operational structures are encoded in the hologram. Preferably, the hologram is a reflective hologram, and is protected by a transparent protective coating located laser-proximal to the hologram. FIG. 26 shows an optical disc assembly containing a reflective hologram 512 which is protected by a transparent protective coating 514. The hologram encodes the operational structures, such as wobble grooves, that are required by the operation of the optical disc reader. When a laser beam 516 is reflected from the hologram physical plane 512, it appears as though the encoded operational structures, such as wobble grooves in a correct orientation, are present at the hologram image plane 518. The hologram image plane 518 can be located substantially confocal with the investigational structure 520. The investigational structure 520 may be positioned on the laser-distal surface 522 of the lens layer 524.

The laser beam may be focused on the image plane 518 which is shared by both the investigational structure 520 and the encoded operational structures. Therefore, light from the image plane 518 may enable the disc reader to generate both the operational signals, such as the signals used for disc tracking, and the investigational signals that are indicative of the presence of the investigational structure. This feature allows the optical disc reader to track the disc and detect the investigational structure concurrently and discriminably. The larger the illuminating laser spot 526 on the hologram, the better the image of the operational structures as appeared in the image plane 518. Therefore, the laser preferably is not tightly focused on the hologram physical plane. Typically, a portion of the hologram physical surface may be sufficient to generate the entirety of the image of the operational structures that are interferometrically encoded in the hologram.

The hologram image plane may be positioned not concurrently with the investigational structure, provided that the operational structures, such as the wobble groove, can be concurrently detectable with the investigational structure. The image plane of the hologram may be either laser-proximal or laser-distal to the investigational structure. In addition, the hologram image plane may be either laser-proximal or laser-distal to the hologram's physical plane.

Preferably, the hologram is replaceable or reversibly attachable to the disc assembly. This permits the hologram to be mass-produced using a high-speed holographic printing process. This also permits the re-use of the hologram or other parts of the disc assembly.

Figure 27:
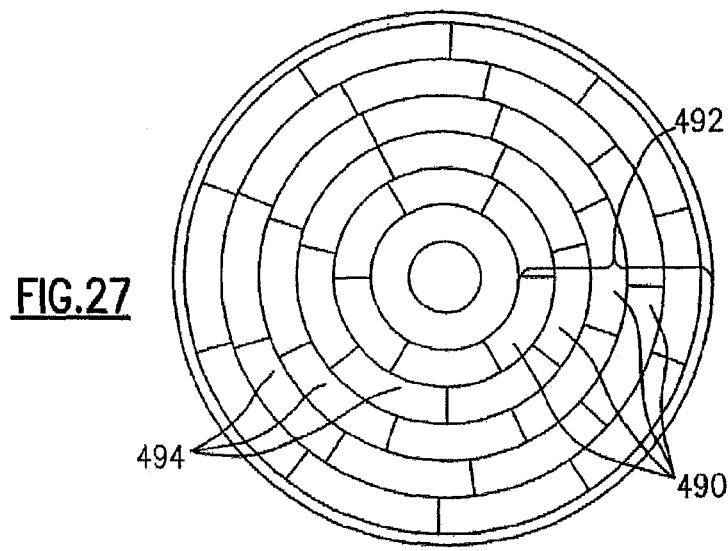
FIG. 27 illustrates the data and surface organization of a zoned constant linear velocity (ZCLV) format.

In another preferred embodiment, the operational structures in the optical disc assembly are configured and organized in accordance with the "zoned constant linear velocity" (ZCLV) format. The ZCLV format is detailed in various industry standards, including the DVD-RAM specification. FIG. 27 schematically illustrates the ZCLV format in a circular disc. The ZCLV disc in FIG. 27 is divided into multiple zones 490 across the range 492. Although only five zones are shown in FIG. 27, actual ZCLV format discs may have different numbers of zones. For instance, the DVD-RAM ZCLV format allows 24 zones.

Each of the zones 490 is divided into multiple sectors 494. Inner zones have fewer sectors than outer zones, because the radii of inner zones are less than the radii of outer zones. The optical disc reader can scan each zone at a constant rate. In addition, the optical disc reader can rotate the ZCLV disc faster when it scans the inner zones than when it scans the outer zone. Therefore, the optical disc reader may maintain a substantially constant scanning rate for all the zones in a ZCLV disc.

Figure 28:
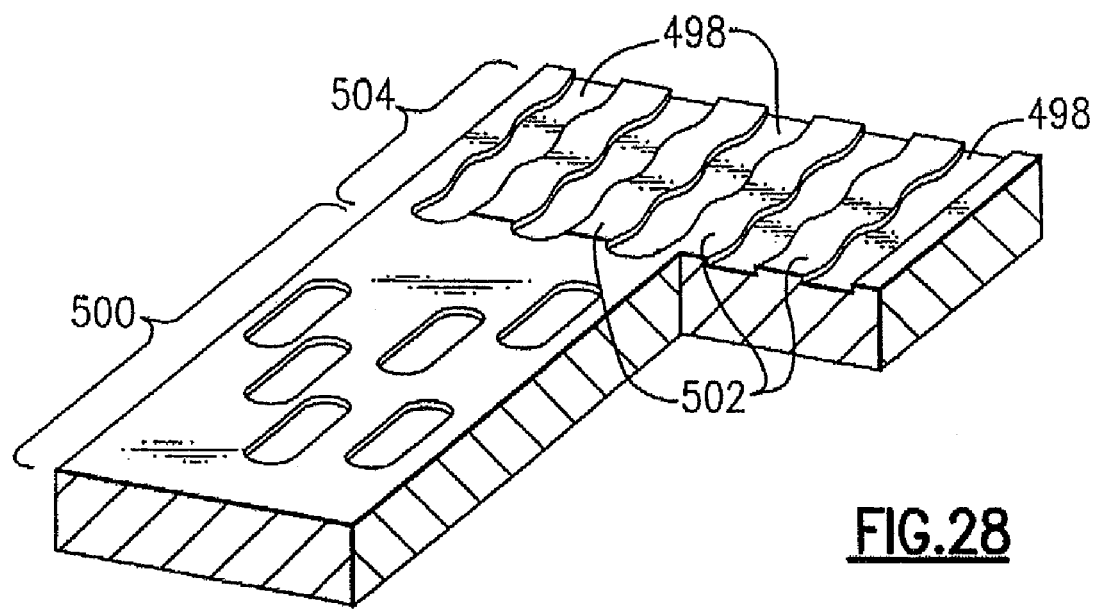
FIG. 28 shows an enlarged perspective view of a portion of a section of a ZCLV disc, wherein the portion has a pre-groove area followed by a wobble groove area.

FIG. 28 shows an enlarged perspective view of a portion of one of the sectors of the ZCLV disc. The operational structures consist of multiple tracks 498 which are arranged radially within the sector. Each track has header information embossed in a "pre-groove" area 500. The pre-groove area is followed by a "wobbled land and groove" area 504 which contains the wobble groove 498 and the wobbled land 502. Operational structures in a ZCLV format may be holographically encoded in a hologram.

Figure 29:
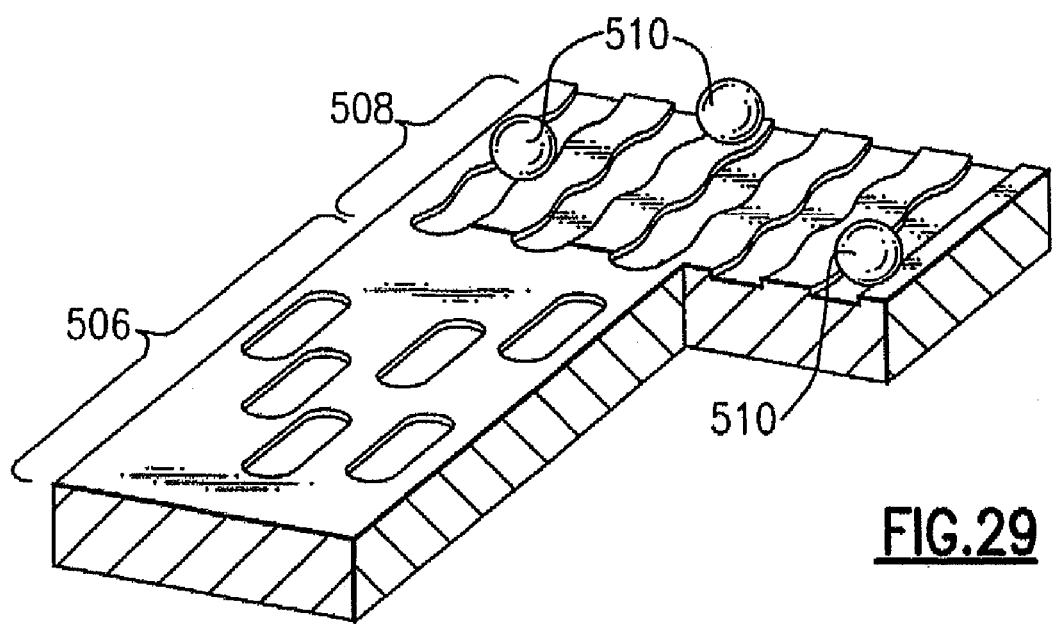
FIG. 29 shows investigational features placed in a section in a ZCLV disc.

FIG. 29 shows a ZCLV-formatted optical disc assembly associated with analytes or investigational structures 510. Analytes or investigational structures 510 may be deposited within the "wobbled land and groove" area 508. The embossed header information in the pre-groove area 506 can be used to store information for identifying or controlling a desired measurement of the analytes or investigational structures 510. Accordingly, different sectors in the same ZCLV disc may be used to perform different measurements or assays.

In one embodiment, the zones in a ZCLV formatted disc can be mastered in such a way as to provide either a highly reflective surface, a partly reflective surface, or a non-reflective surface. In each case, the pre-header information can provide tracking and location information. The pre-header information may also provide identification information for the nature of the zone. In addition, the pre-header information may encode information relating to the software or firmware that is applied to the zone. The characteristics of the investigational structures (such as their reflectivity, absorptivity, or transmissivity) can be determined by the disc laser as it scans over each zone.

In a preferred embodiment, the optical disc assembly includes a semi-reflective layer which is both transmissive and reflective to the laser light. The semi-reflective layer is usually a thin layer of reflective or semi-reflective material, such as silicon, tellurium, selenium, bismuth, aluminum, silver, copper or other suitable metals or alloys. The thickness of the layer may range from 10 nm to 100 nm. The reflectivity of the semi-reflective layer may range from about 18% to 30%. The reflectivity may also range from about 30% to 40%. The semi-reflective layer may be used to coat operational structures. Whereas the reflectivity of the semi-reflective layer is low, for instance, below about 30%, a CD-RW reader or a DVD reader preferably is used to read the operational structures that are coated with the semi-reflective layer.

Figure 30:
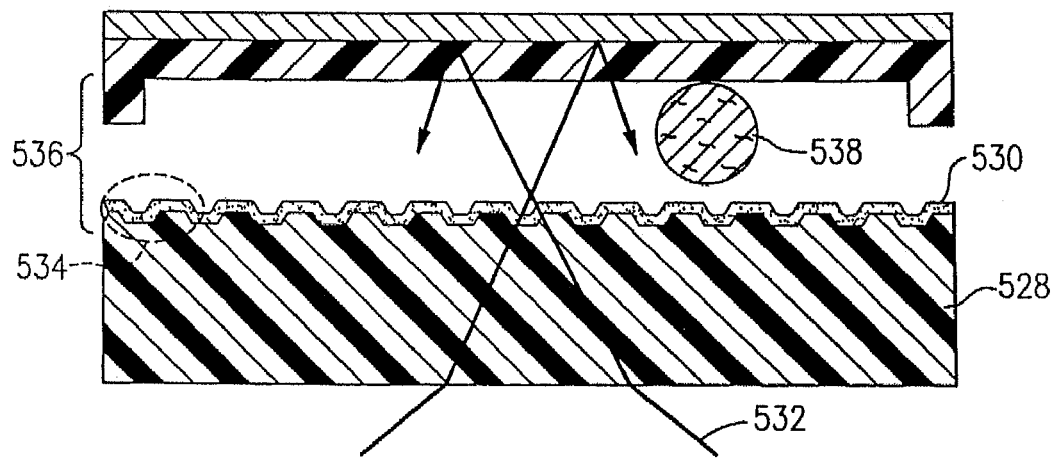
FIG. 30 is an example of a forward disc, wherein the operational structures are coated with a semi-reflective layer, and investigational features are held laser-distal to the semi-reflective layer.

FIG. 30 illustrates a forward optical disc assembly which includes a semi-transmissive, semi-reflective layer. The semi-transmissive, semi-reflective layer 530 is placed on the operational structures which are embossed in the laser-distal surface of the operational layer 528. Reference numeral 534 shows an operational structure coated with the layer 530. The reflectivity of the layer 530 can return sufficient light to render the operational structures detectable by the disc reader. The laser beam 532 can also pass through the layer 530 to enter the analyte section 531 which is configured to hold the analyte 538. The analyte section 533 and the analyte 538 are within the laser's focal zone 536. The laser beam 532 can be reflected back from another reflective layer 533 which is laser-distal to the semi-transmissive, semi-reflective layer 530. This latter reflected light may carry signals indicative of the presence of the analyte. The laser's focus is able to roam within the focal zone 536.

FIG. 31 illustrates a forward transmissive pass-through disc assembly which permits the laser light 540 to pass through the top refractive layer 542 to a top detector. The laser 540 is focused by the lens layer 544, which is also the operational layer. The operational features are coated with a partly reflective and partly transmissive layer 548. Reference numeral 546 shows a coated operational feature. The analyte 550 is placed in the analyte section 552 which is situated between the lens layer 544 and the top refractive layer 542. Samples including solutions may be directed to and expelled from the analyte section 552 through channels or other means. The laser's focus, driven by the laser's focusing servo, can roam within the focal zone 554. The coated operational features and the analyte 550 are both placed within the focal zone and can be detected concurrently and discriminably.

In accordance with another aspect of the present invention, the optical disc assembly may contain channels or chambers capable of transporting analytes, reactive components or mediums to and from the analyte section. Analytes and other components can be mixed within these channels or chambers. Preferably, the analyte section also contains at least one chamber or channel which is capable of holding the analytes for investigation. More preferably, the operational surface contains a cut-away area which may be either laser-proximal or laser-distal to the analyte section and which may be adjacent to the analyte section. Most preferably, the analyte section includes a cut-away area as one surface.

Figure 32:
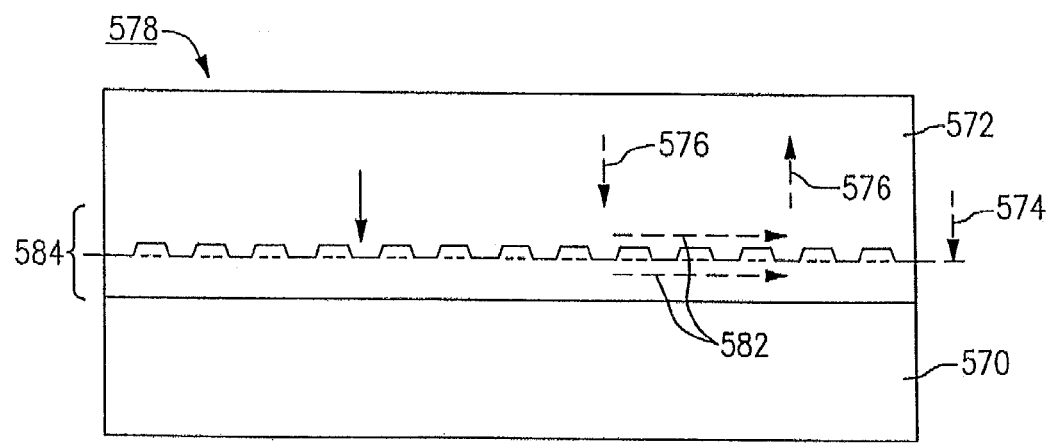
FIG. 32 depicts a reverse optical disc assembly which includes fluidic channels placed either above or below the operational surface.

FIG. 32 demonstrates a reverse disc assembly 578 including fluidic channels. The lens layer 570 is laser-proximal to the operational layer 572. The operational structures are embossed in the laser-proximal surface of the operational layer 572. The plane 574 depicts the plane upon which the operational surface and the operational structures are located. The operational layer 572 contains channels 576 through which analytes or investigational structures can enter or exit the analyte section. The analyte section includes the channel 582 which can be located either laser-proximal or laser-distal to the operational surface. The arrows associated with 576 and 582 indicate the direction of fluidic flow in the channels. The channel 582 and the operational surface are located within the focal zone 584.

Figure 33:
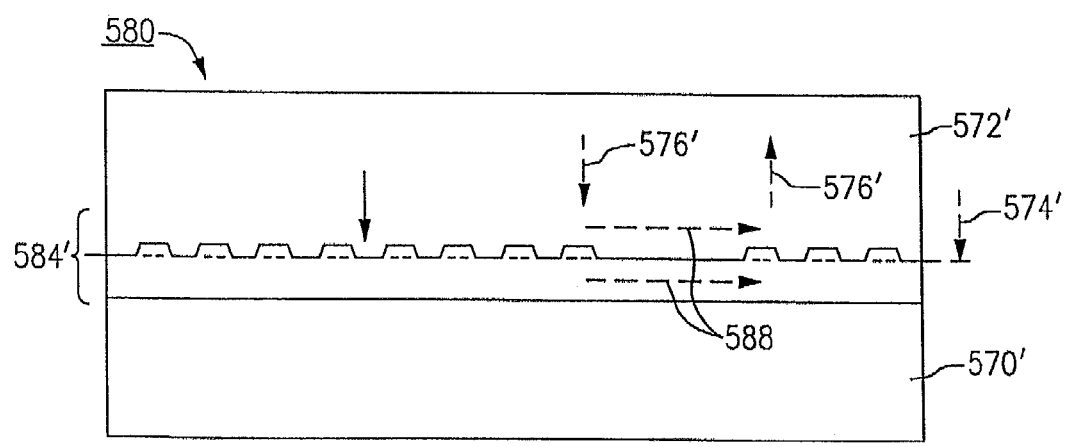
FIG. 33 shows another reverse optical disc assembly in which the operational surface has a cut-away area and fluidic channels are placed either above or below the cut-away area.

FIG. 33 shows another reverse optical disc assembly 580 in which the analyte section, which includes channel 588, is either laser-proximal or laser-distal to a cut-away area. The operational surface is position on the plane 574'. The cut-away area is in the operational surface which is the laser-proximal surface of the operational layer 572'. The cut-away area preferably lacks operational structures or reflective coatings. Channels 576' direct the fluidic flow to and from channel 588. The operational surface, the cut-away area and channel 588 are within the focal zone 584'. 570' denotes the lens layer.

Figure 34:
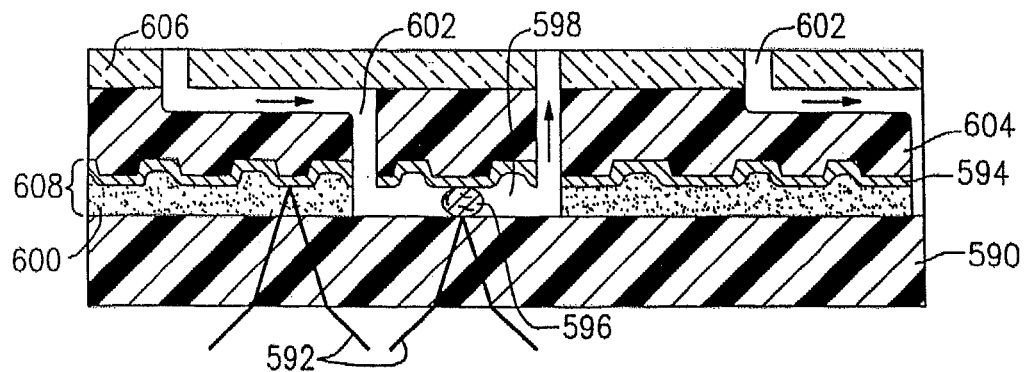
FIG. 34 illustrates an example of a reverse optical disc assembly which includes channels and an analyte chamber.

FIG. 34 depicts a preferred reverse optical disc assembly. The lens layer 590 focuses the laser beam 592 either on the reflective layer 594 or on the analyte 596. The reflective layer 594 coats the operational structures located at the laser-proximal surface of the operational layer 604. The analyte 596 resides in the analyte section which consists of the chamber 598. The chamber 598 is laser-proximal to the operational structures and laser-distal to the lens layer. The adhesive layer 600 binds the operational layer 604 to the lens layer 590. The channels 602 are etched into the operational layer 604. Analytes can enter and leave the analyte section 598 through channels 602. The operational layer 604 is covered by the cover 606. The operational structures and the analyte section are with the laser's focal zone 608.

Figure 35:
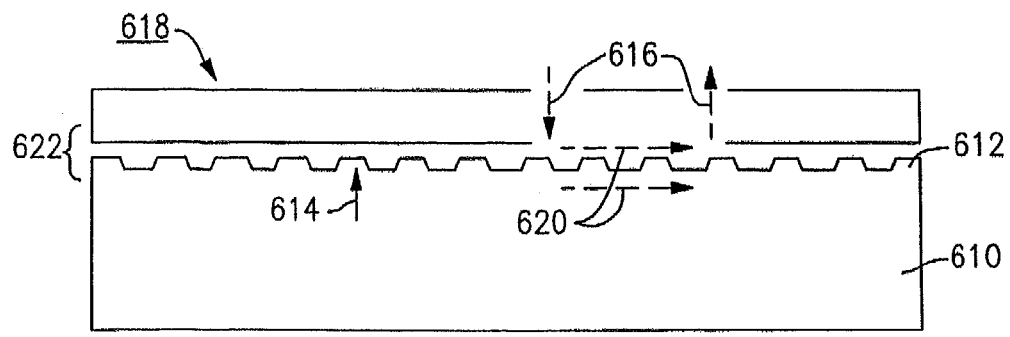
FIG. 35 depicts a forward optical disc assembly which includes fluidic channels placed either above or below the operational surface.

FIG. 35 demonstrates a forward optical disc assembly 618 which includes fluidic channels 616 and 620. The operational layer 610 serves as a lens layer and is capable of focusing the laser beam 614 on the operational structures 612. The operational structures 612 are located at the laser-distal surface of the operational layer 610. Channels 616, contained in the cover, can introduce analytes into the analyte section which includes the channel 620. The channel 620 can be either laser-proximal or laser-distal to the operational structures. Both the operational structures and the channel 620 are within the focal zone 622.

Figure 36:
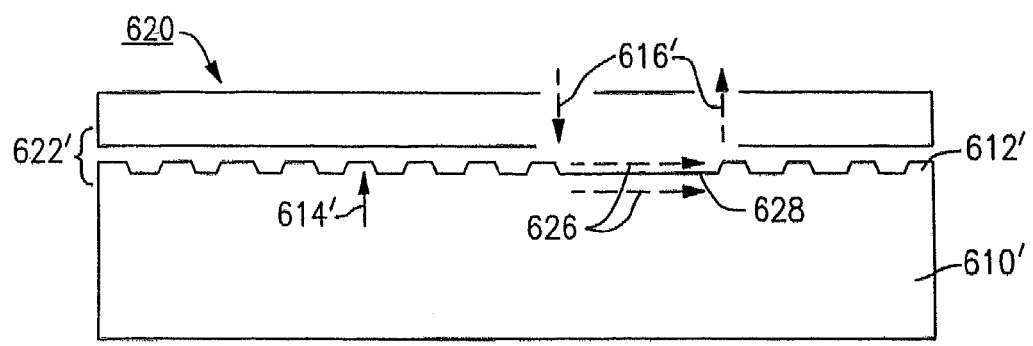
FIG. 36 shows another forward optical disc assembly in which the operational surface has a cut-away area and fluidic channels are placed either above or below the cut-away area.

FIG. 36 shows a forward disc assembly 621 including a cut-away area 628 in the operational surface. The cut away area 628 is in the laser-distal surface of the operational layer 610', and preferably lacks operational structures or reflective coatings. Other areas in the laser-distal surface of the operational layer 610' are contained with the operational structures 612'. The channel 626 in the analyte section can be either laser-proximal or laser-distal to the cut-away area 628. The focal zone 622' encompasses the operational structures 612', the cut-away area 628, and the channel 626.

FIG. 37 illustrates a preferred embodiment of a forward optical disc assembly which includes analyte channels 666. The analyte channels 666 are in or immediately above the lens layer 658. These channels are connected to the analyte section 668. The lens layer 658 is attached to the operational layer 662 through the adhesive layer 660. The lens layer 658 is laser-proximal to the operational layer 662. The operational structures at the laser-distal surface of the operational layer 662 are coated with a semi-reflective, semi-transmissive layer 664. The analyte section 668 is configured to receive analytes 670, and is located laser-distal to the semi-transmissive layer 664 and laser-proximal to another reflective layer 678. The reflective layer 678, which preferably is fully reflective, is laser-proximal to the cover 680. Laser beam 676 can pass through the lens layer 658, the adhesive layer 660, the operational layer 662 and the semi-transmissive layer 664 to focus on the analytes 670 or the reflective layer 678. The laser 676 can be reflected from the reflective layer 678. The laser focal point can move across the focal zone 674. Light reflected from layer 664 may carry operational information, whereas light reflected from layer 678 may carry investigational information.

Figure 38:
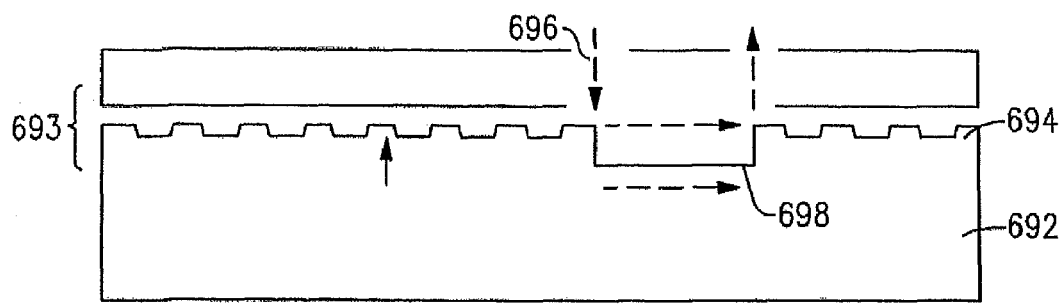
FIG. 38 shows a forward disc with channels placed above or below a cut-away area.

FIG. 38 schematically demonstrates another embodiment of a forward optical disc assembly. The analyte section includes an analyte channel which can be located either laser-proximal or laser-distal to the cut-away area 698. The cut-away area 698 is at the laser-distal surface of the operational layer 692. The cut-away area preferably lacks operational structures or reflective coatings. Other areas in the laser-distal surface of the operational layer 692 include the operational structures 694. In FIG. 38, the cut-away area 698 is laser-proximal to the plane upon which the operational structures reside. Channels 696 are created in the cover layer of the disc assembly. Analytes or reaction components can enter or exit the analyte channel through channels 696. The laser's focal zone 693 encompasses the operational structures 694, the cut-away area 698, and the analyte channel. One of skill in the art will appreciate that, in view of FIG. 38, the cut-away area 698 may also be located laser-distal to the plane upon which the operational structures are disposed.

Figure 39:
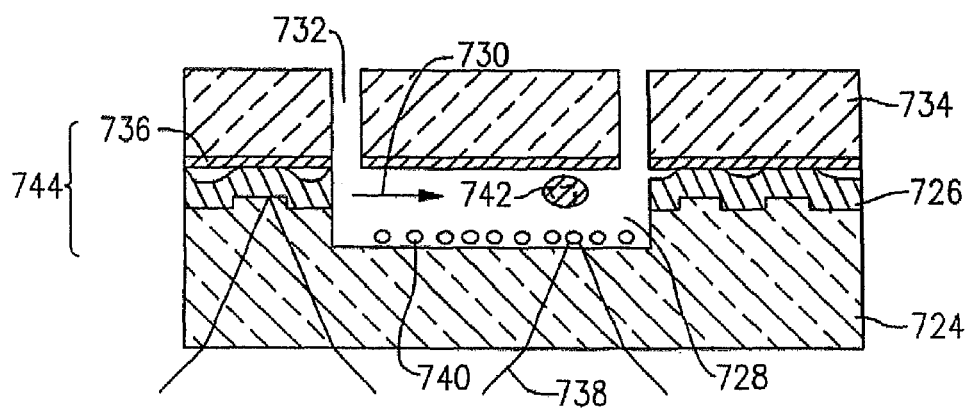
FIG. 39 shows a forward disc assembly having a cut-away area.

FIG. 39 illustrates a preferred embodiment of a forward optical disc assembly including a cut-away area. The cut-away area is laser-proximal to the plane upon which the operational structures reside. The operational structures are positioned at the laser-distal surface of the operational layer 724, and are coated by a reflective or semi-reflective layer 726. The cut-away area preferably lacks operational structures or the coating 726. The analyte section includes a chamber 728 which is etched into the operational layer 724. The cut-away area constitutes the most laser-proximal surface of the chamber 728. Fluidic flow 730 enters into the chamber 728 through channels 732 which cut through the cover layer 734. A reflective layer 736 is located laser-proximal to the layer 734 but laser-distal to the operational structures. The laser 738 encounters and detects the first analytes 740 which are deposited on the cut-away area. The fluidic flow 730 may also mix the first analytes 740 with the second analyte 742. The interaction between the analytes 740 and the analyte 742 may generate detectable signals. The laser's focal zone 744 encompasses the chamber 728. As appreciated by one of skill in the art, channels 732 may be created with the operational layer 724.

In one embodiment, the disc is a hybrid disc in that the operational surface includes at least two different formats of operational structures. For instance, the operational surface may include operational structures in a CD format as well as operational structures in a DVD format. The disc reader may read both formats. Data facilitating or regulating the disc reader to read different formats of operational structures may be encoded or embossed in the disc.

In a preferred embodiment, data other than operational structures can be encoded or embossed in the operational surface or other surfaces in the disc assembly. These data may provide control information for the disc reader to read or detect the investigational structures. These data may regulate the measurement of investigational structures, for instance, by controlling valves which can manage fluidic flows in a fluidic circuit. These data, as well as the operational structures or other information, may be written to the disc before or after the investigational structures are read or detected.

The disc assembly may be used for detecting biological suspensions such as blood, urine, saliva, amniotic fluid, cerebrospinal fluid, synovial fluid, pleural fluid, pericardial fluid, perintoneal fluid. Environmental and chemical samples may also be assayed using the disc assembly. The disc assembly may include embossed features, placed features or etched features.

The disc assembly may be a null type disc, a modified disc based on industry standard disc, such as a modified CD-R or a modified CD, or a disc based on a custom format. Preferably, the disc assembly does not have the dye layer as used in a CD-R or a CD-RW disc.

In one embodiment, data used to identify the type of the disc assembly can be encoded in the disc assembly. For instance, a disc identification number (DIN) may be digitally encoded in the disc to describe the type of the operational layer, such as a forward wobble disc or a reverse wobble disc. The DIN may also be used to describe the design of the analyte section, the adhesive layer or the cover of the disc.

In another embodiment, the disc assembly includes an operational layer, an adhesive layer and a cover. The operational layer, the adhesive layer, or the cover of the disc may contain channels, cavities, slots, openings, or holes. The thickness of the adhesive layer may be between 25 and 500 micrometers, including within the range of about 25 micrometers to 100 micrometers, such as 50 micrometers. The adhesive material may be pressure sensitive, and can be made from acrylic or silicone. The cover layer may be coated with reflective materials such as gold.

An analyte chamber may be located within the adhesive layer. The operational layer or the cover may contain channels that are connected to the analyte chamber. Analytes, components reactive thereto or mediums can be introduced through these channels to the analyte chamber.

Figure 40:
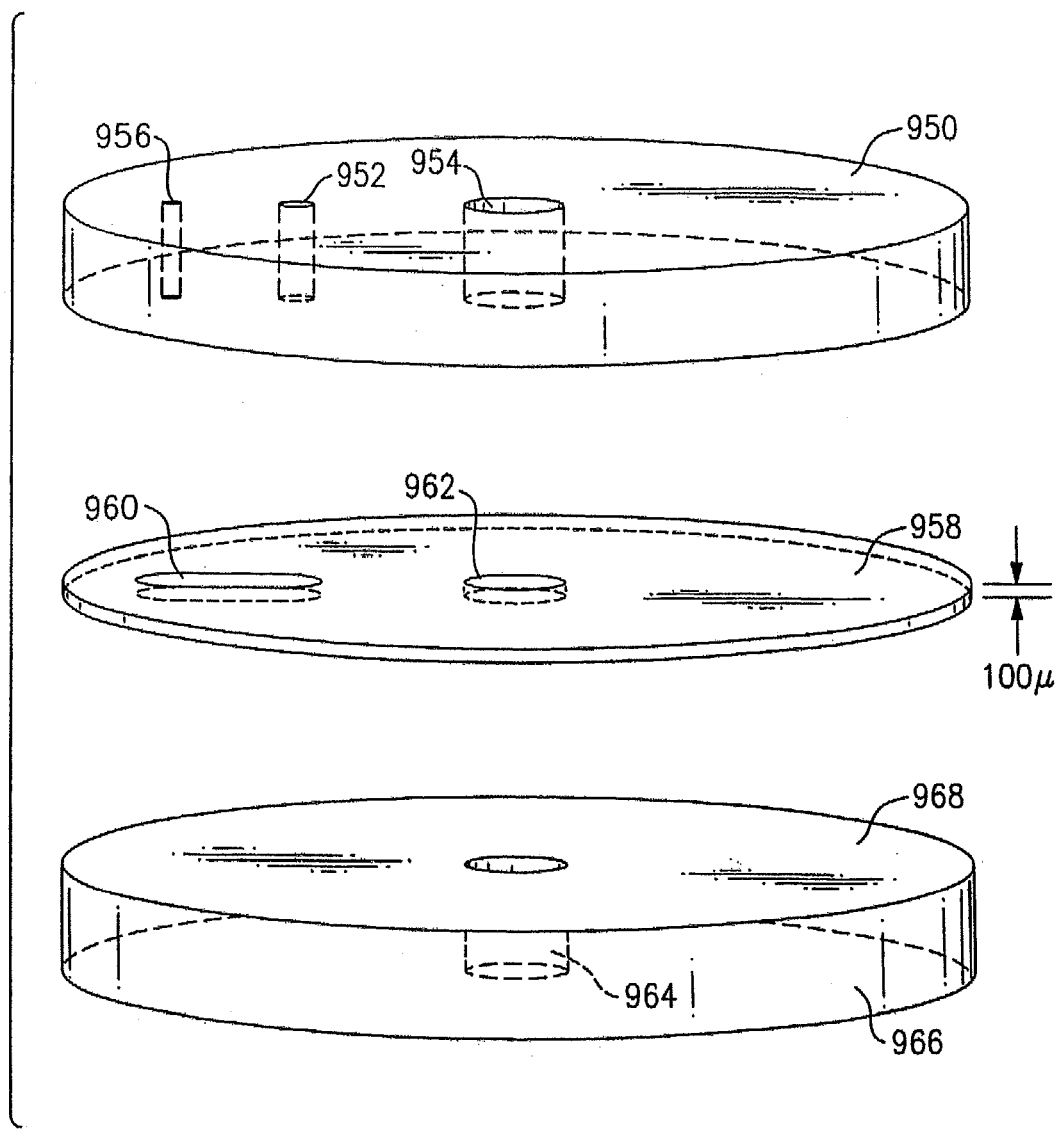
FIG. 40 illustrates an exploded perspective of the principle layers in a forward disc assembly according to one embodiment of the present invention.

FIG. 40 illustrates an exploded perspective view showing the principle layers of a forward disc assembly according to one embodiment the present invention. The operational layer 966 is laser-proximal to the adhesive layer 958 which is laser-proximal to the cover 950. The operational surface 968 is coated with a semi-reflective, semi-transmissive layer. The operational layer 966, the adhesive layer 958 and the cover 950 includes a central hole 964, 962 and 954, respectively. The disc assembly can be coupled to a disc reader through these holes, for example, by clamping to a motor shaft. The adhesive layer includes an opening 960, which forms an analyte chamber when these layers are assembled together. The adhesive layer has a depth of about 100 micrometers. Investigational structures can be manipulated or retained in the analyte chamber formed by the opening 960. The cover 950 includes the ports 952 and 956. When the disc is assembled, these channels are connected to the analyte chamber 960. Investigational structures or other reaction components may enter or exit from the chamber 960 through the ports 952 and 956. Both the operational layer and the cover layer may be made from polycarbonate. The laser beam may pass through the disc assembly and be read by a top detector. Alternatively, a reflective layer may be coated at the laser-proximal surface of the cover 950 so that the laser beam can be reflected back therefrom.

As appreciated by one of skill in the art, a reverse wobble disc assembly can be similarly constructed as shown in FIG. 40. In addition, channels or openings, through which investigational structures or reaction components can be introduced into the analyte section, may be created in the operational layer. Operational structures may be created in the laser-proximal surface of the cover layer 950.

Figure 41:
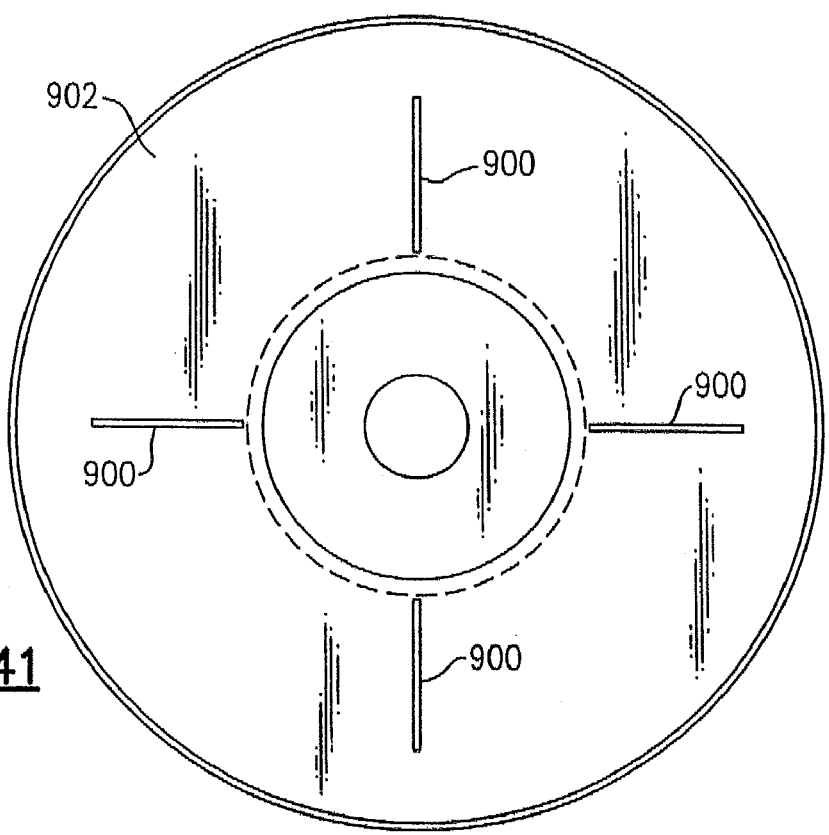
FIG. 41 shows a design of an operational layer.
Figure 42:
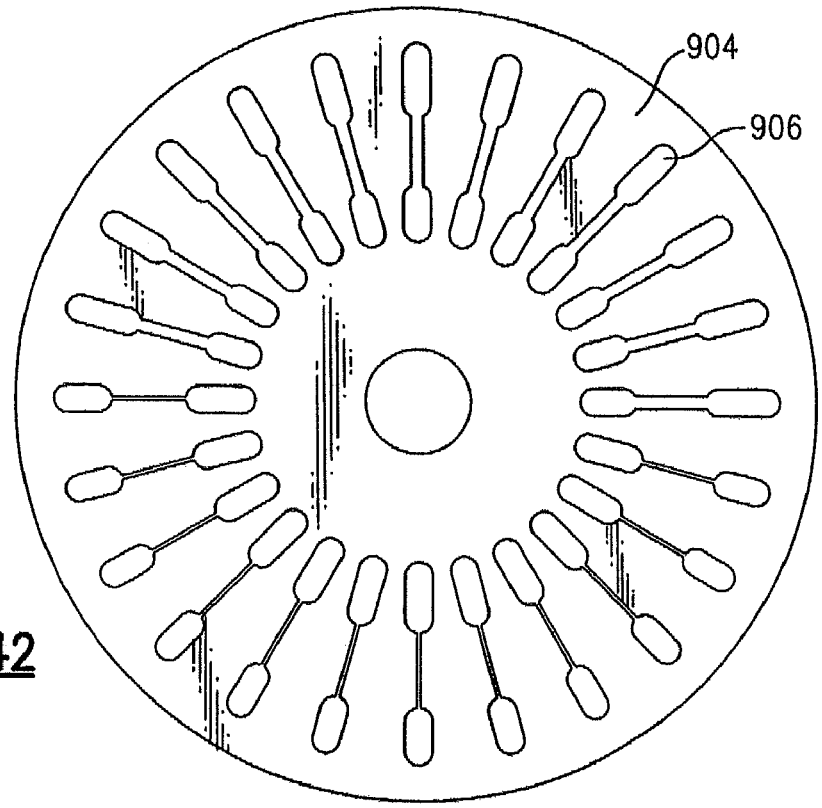
FIG. 42 shows a design of an adhesive layer.

Channels, cavities, inlet and vent ports, or other structures in the operational layer, the adhesive layer or the cover may be in a variety of configurations. FIG. 41 shows an operational layer 902 which has four slots 900. FIG. 42 shows an adhesive layer 904 which has a series of openings 906. These openings can form analyte chambers in the assembled disc. These different chambers may be connected to different channels located in either the cover layer or the operational layer. The assembled disc may perform different assays in different analyte chambers.

Data encoding design information that identifies the type of the disc assembly may be stored in the disc assembly and readable by the disc reader. Such information may also be printed on a surface of the disc assembly. For instance, a disc identification number (DIN) can be used to identify the type of the disc assembly. The number may include alphanumeric characters that are subdivided into different fields. One field may describe the main specifications of the operational layer. The main specifications include whether the disc is a reverse disc or a forward disc, and the particular disc design type for the operational layer. The main specifications may also include an identification number for the master of the operational layer. A second field of the DIN may represent various modifications or other variables of the operational layer. The variables include the placement of the cut-away areas and the number of analyte chambers. In addition, the second field of the DIN may describe the position of the adhesive layer or techniques or materials used in making the disc assembly. The designs of the cover layer may also be described in the second field. A third field may include, which can be used to identify each disc. This serial number may be in the order of manufacture of the disc.

It should be understood that the above-described embodiments are given by way of illustration, not limitation. Various changes and modifications within the spirit and scope of the present invention will become apparent to those skilled in the art from the above description. In addition, the reader's attention is directed to the provisional applications from which the present application claims priority. The contents of all these provisional applications are incorporated herein by reference.

What is claimed is:

1. An apparatus for focusing light on a portion of an optical disc, the optical disc comprising at least one analyte section for receiving an analyte for analysis by the apparatus, the apparatus comprising:
    a light source configured to emit light;
    a lens configured to receive the light on a first side of the lens and to direct the light out of a second side of the lens towards the optical disc such that the light is focused at a focal point;
    a coil attached to the lens, wherein the coil and lens assembly are moveably attached to the apparatus so that a position of the focal point with reference to the disc may be adjusted by moving the coil and lens assembly in a direction that is substantially perpendicular to a plane of the optical disc; and
    a magnet positioned proximate the lens and configured to cause the coil and the lens attached to the coil to move corresponding to an adjustable range of magnetic strength of the magnet, wherein the magnetic strength is adjustable in response to an amount of reflected laser light from the optical disc so as to maximize the amount of reflected laser light as the position of the focal point on the optical disc is adjusted.

2. The apparatus of claim 1, wherein the optical disc comprises:
    a first layer comprising optically readable structures impressed therein; and
    a second layer, and wherein the analyte section includes a first chamber which is positioned between the first layer and the second layer and which is capable of receiving the analyte that can be detected by the optical disc reader.

3. The apparatus of claim 2, wherein at least one of the first layer and the second layer includes a first channel connecting to the first chamber.

4. The apparatus of claim 3, wherein the first channel includes a valve which can be regulated by optically readable data encoded in the optical disc assembly.

5. An apparatus for adjusting a position of a lens in relation to an optical biodisc, the apparatus comprising:
    a lens configured to focus light incident on the lens towards a focal point; and
    a movement mechanism configured to adjust a position of the lens with respect to the optical biodisc such that as a distance between the lens and the optical biodisc changes, the position of the focal point on the optical biodisc correspondingly changes, the movement mechanism being configured to position the focal point at a desired depth of the optical bio disc for analysis of one or more investigative features.

6. The apparatus of claim 5, wherein the movement mechanism is configured to adjust a position of the lens with respect to the optical biodisc in response to an amount of light that reflects from the optical biodisc towards the apparatus.

7. The apparatus of claim 6, wherein the apparatus comprises an optical detector in communication with the movement mechanism, the optical detector configured to determine an amount of light reflected from the optical biodisc.

8. The apparatus of claim 5, wherein the desired depth of the optical bio disc comprises a layer of the optical bio disc containing investigational features.

9. The apparatus of claim 5, wherein the desired depth of the optical bio disc comprises a layer of the optical bio disc that is most highly reflective.

10. The apparatus of claim 5, wherein the movement mechanism comprises:
    a coil attached to the lens, wherein the coil and lens assembly are moveably attached to the apparatus so that a position of the focal point with reference to the disc may be adjusted by moving the coil and lens assembly in a direction that is substantially perpendicular to a plane of the optical disc; and
    a magnet positioned proximate the lens and configured to cause the coil and the lens attached to the coil to move corresponding to an adjustable range of magnetic strength of the magnet, wherein the magnetic strength is adjustable in response to an amount of reflected laser light from the optical disc so as to maximize the amount of reflected laser light as the position of the focal point on the optical disc is adjusted.

11. A method of focusing light on a portion of an optical disc, the optical disc comprising at least one analyte section for receiving an analyte for analysis by the apparatus, the method comprising:
  emitting light from a light source;
  focusing the emitted light towards the optical disc such that the light is focused at a focal point between a top and bottom surface of the optical disc;
  adjusting a position of the focal point between the top and bottom surface of the optical disc by adjusting a position of a lens with reference to the optical disc;
  controlling the adjusting in response to an amount of light reflected from the optical disc so as to maximize the amount of reflected laser light by adjusting the position of the focal point to be at a most reflective position between the top and bottom surfaces of the optical disc.

12. A hologram that is removably attachable to an optical bio-disc, the hologram comprising:
  a planar substrate comprising encoded operational structures, the hologram being configured so that a laser beam reflected from the substrate causes the encoded operational structures to be readable at an image plane that is spaced away from the planar substrate, the image plane being substantially confocal with a layer of the optical bio-disc comprising one or more investigational features.

13. The hologram of claim 12, wherein the optically readable structures comprise encoded tracking information.

14. The hologram of claim 12, wherein the optically readable structures comprise speed information enabling an optical disc reader to rotate the optical disc assembly at a speed that is determinable from said speed information.

15. The hologram of claim 12, wherein the optical bio-disc comprises an analyte section capable of receiving the one or more investigational features, and wherein at least a portion of the image plane is location within the analyte section.

16. The hologram of claim 15, wherein the investigational features comprise analytes.

17. The hologram of claim 12, wherein the hologram is configured for engagement with multiple optical bio-discs.

18. The hologram of claim 12, wherein the hologram is reflective.

19. The hologram of claim 12, wherein the hologram is configured to releasably engage with the optical bio-disc such that the investigational features on the optical bio-disc are positioned within 15 micrometers from an image plane of the hologram.

20. A method of analyzing investigational features contained on a bio-disc, the method comprising:
  positioning a hologram on the bio-disc, the hologram comprising encoded operational structures that are usable by a disc reader to control operations of the disc reader, the hologram being configured so that a laser beam reflected from the hologram causes the encoded operational structures to be readable by the disc reader at an image plane that is substantially confocal with a layer of the bio-disc comprising one or more investigational features, wherein the hologram is removably attached to the bio-disc;
  emitting a laser light towards the bio-disc so that the light has a focal point proximate a layer of the bio-disc containing the investigational features;
  determining the encoded operational structures in response to detection of an image of the encoded operational structures at the image plane; and
  determining characteristics of the one or more investigational features located substantially confocal to the image plane in response to reflection of at least a portion of the light from the investigational features.

21. The method of claim 20, wherein the encoded operational structures comprise a wobble groove.

22. The method of claim 20, wherein the encoded operational structures are in a zoned constant linear velocity format.

* * * * *